(12) United States Patent
Fischer

(10) Patent No.: US 10,543,229 B2
(45) Date of Patent: Jan. 28, 2020

(54) DIETARY SUPPLEMENT COMPOSITION AS A PROPHYLACTIC AND TREATMENT FOR SKIN DISEASES SUCH AS ECZEMA AND PSORIASIS AND THE LIKE AND METHOD OF TREATMENT

(71) Applicant: Karen Jane Fischer, Randwick (AU)

(72) Inventor: Karen Jane Fischer, Randwick (AU)

( * ) Notice: Subject to any disclaimer, the term of this patent is extended or adjusted under 35 U.S.C. 154(b) by 0 days.

(21) Appl. No.: 14/617,856

(22) Filed: Feb. 9, 2015

(65) Prior Publication Data

US 2015/0150904 A1    Jun. 4, 2015

Related U.S. Application Data

(63) Continuation-in-part of application No. PCT/AU2013/000873, filed on Aug. 8, 2013.

(30) Foreign Application Priority Data

Aug. 8, 2012 (AU) ................. 2012903404

(51) Int. Cl.
| | | |
|---|---|---|
| A61K 33/00 | (2006.01) | |
| A61K 31/00 | (2006.01) | |
| A23L 33/00 | (2016.01) | |
| A61K 33/06 | (2006.01) | |
| A61K 31/198 | (2006.01) | |
| A61K 31/355 | (2006.01) | |
| A61K 31/375 | (2006.01) | |
| A61K 31/4188 | (2006.01) | |
| A61K 31/4415 | (2006.01) | |
| A61K 31/51 | (2006.01) | |
| A61K 31/525 | (2006.01) | |
| A61K 31/593 | (2006.01) | |
| A61K 31/714 | (2006.01) | |
| A61K 33/30 | (2006.01) | |
| A61K 31/455 | (2006.01) | |
| A61K 33/24 | (2019.01) | |

(52) U.S. Cl.
CPC ............ *A61K 33/06* (2013.01); *A61K 31/198* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/593* (2013.01); *A61K 31/714* (2013.01); *A61K 33/24* (2013.01); *A61K 33/30* (2013.01)

(58) Field of Classification Search
None
See application file for complete search history.

(56) References Cited

U.S. PATENT DOCUMENTS

| | | | |
|---|---|---|---|
| 4,599,152 A | * | 7/1986 | Ashmead ................. C25B 3/02 |
| | | | 205/435 |
| 4,806,525 A | | 2/1989 | Morganti |
| 2002/0132800 A1 | * | 9/2002 | Popp ........................ A23L 1/29 |
| | | | 514/168 |
| 2004/0213829 A1 | | 10/2004 | Coleman et al. |
| 2006/0246200 A1 | | 11/2006 | Parvez |
| 2010/0021573 A1 | | 1/2010 | Gonzalez et al. |

FOREIGN PATENT DOCUMENTS

| | | |
|---|---|---|
| WO | 1998047497 A2 | 10/1998 |
| WO | 1999043329 A1 | 9/1999 |
| WO | 2002012882 A2 | 2/2002 |
| WO | 2005067972 A1 | 7/2005 |
| WO | 2006060578 A2 | 6/2006 |
| WO | 2007057748 A2 | 5/2007 |

OTHER PUBLICATIONS

International Search Report and Written Opinion, dated Oct. 21, 2013.

* cited by examiner

*Primary Examiner* — Hasan S Ahmed
*Assistant Examiner* — Frank Choi
(74) *Attorney, Agent, or Firm* — Walter Haverfield LLP; James J. Pingor

(57) ABSTRACT

A dietary supplement composition as a prophylactic and treatment for skin diseases such as eczema and psoriasis and the like, the composition comprising a phase II liver detoxification component having glycine, and magnesium, wherein glycine and magnesium are present in the supplement composition in a ratio of between about 20:1 and 20:8.

5 Claims, 4 Drawing Sheets
(3 of 4 Drawing Sheet(s) Filed in Color)

DIETARY SUPPLEMENT COMPOSITION AS A PROPHYLACTIC AND TREATMENT FOR SKIN DISEASES SUCH AS ECZEMA AND PSORIASIS AND THE LIKE AND METHOD OF TREATMENT

CROSS-REFERENCE TO RELATED APPLICATIONS

This application claims the benefit of the filing date of AU provisional patent application no. 2012903404 filed on 8 Aug. 2012 and having a title 'A method, use, and dietary supplement composition for at least treating an atopic or non-atopic disorder in a patient', which is incorporated herein by reference, and is a Continuation-in-Part application of International patent application no. PCT/AU2013/000873 filed on 8 Aug. 2013 and having a title 'A method, use, and dietary supplement composition for at least treating an atopic or non-atopic disorder in a patient', which is also incorporated herein by reference.

BACKGROUND

A normal skin barrier is thick and in the stratum corneum the corneodesmosomes are intact and the outermost layers of dead skin cells flake off in a barely detectable manner, as the outermost binders snap and release the unwanted cells. However, in atopic eczema or dermatitis, and other dry skin disorders, the skin barrier is typically thinner than normal so the skin's protective and regulatory capacities are compromised. As the skin barrier breaks down, cracks appear in the skin barrier which allows allergens such as dust mites and bacteria to enter the skin, thereby causing a worsening of the skin disorder.

In Australia, about six million people suffer from eczema and about six hundred thousand people have psoriasis. In the USA, over 32 million people have eczema and 7.5 million suffer from psoriasis. Present statistics suggest that eczema sufferers have tripled in the past 30 years and one in five children suffer. It is generally accepted in medical opinion, that there is currently no known cure for eczema or psoriasis, and symptoms can endure a sufferer's lifetime.

Skin diseases such as eczema, psoriasis and dermatitis can be incredibly painful and embarrassing, and lifelong. Eczema symptoms generally include incredible itchiness and sufferers typically have poor sleep and liken it to "sleeping on an ants' nest." Eczema is typically characterized by itchy, dry, red, flaky patches of skin, which appear most commonly on the face, neck, elbows, wrists, knees, behind the ears, and on the scalp. Psoriasis is a chronic skin disease where skin cells build up and form thick patches which are itchy and unsightly. In numerous instances, children and infants suffering from congenital eczema have been reported with significant delayed development in speech and growth.

Present treatments for eczema and psoriasis include the application of moisturizers between four to six times daily. Healthcare professionals prescribe topical hydrocortisone however this treatment is usually discontinued after seven days, and it is considered a risk for use on children under two years or on irritated or broken skin. Eczema is irritated and broken skin, and sufferers are often under two years. In any case it is known that topical steroids do not cure eczema and often they are applied for years which can result in permanent thinning of the skin, stretch marks, cataracts (if used near eyes) and Cushing's syndrome.

Topical immunosuppressants (topical calcineurin inhibitors) are sometimes prescribed to reduce eczema and psoriasis symptoms. Such products however do not provide a cure, and medical practitioners are hesitant to prescribe immunosuppressants due to documented side-effects. In particular, in 2006, the U.S. Food and Drug Administration warns on product packaging that "a small number of malignancies (skin cancer and lymphoma) have been reported in patients using topical calcineurin inhibitors."

Typically, more than half of eczema sufferers present with salicylate sensitivity, which worsens after ingesting salicylate-containing foods (found in many healthy foods, fruits and vegetables, sauces and juices). Salicylate- and multiple chemical-sensitivities reduce a person's quality of life and long term adherence to low salicylate diets can be restrictive and can lead to nutritional deficiencies. Eczema sufferers are also known to have elevated histamine levels in the blood combined with a reduced capacity to detoxify these histamines.

Certain nutrients are considered to be of significant benefit to patients suffering from skin disorders such as eczema. However, it is oftentimes difficult to achieve the right balance of nutrients in a patient's diet in order to prevent and/or treat such disorders. This is particularly true in cases where certain nutrients included in a patient's diet can compete for absorption with other nutrients, thereby negating the benefits of the other nutrients.

One object of the present invention is therefore to ameliorate one or more of the deficiencies of the prior art, or to at least provide a useful alternative to improved treatment for skin diseases such as eczema, psoriasis and dermatitis.

It is to be understood that, if any prior art information is referred to herein, such reference does not constitute an admission that the information forms part of the common general knowledge in the art, in Australia or any other country.

BRIEF DESCRIPTION

This brief description is provided to introduce a selection of concepts in a simplified form that are described below in the detailed description. This brief description is not intended to be an extensive overview of the claimed subject matter, identify key factors or essential features of the claimed subject matter, nor is it intended to be used to limit the scope of the claimed subject matter.

The present invention relates to skin diseases including eczema, psoriasis and the like disorders, and in particular to a dietary supplement composition for treating symptoms of skin diseases and for use as a prophylactic treatment and method of treatment of such skin diseases with such composition.

The invention has been developed primarily for use in at least treating atopic and non-atopic eczema, psoriasis, and dermatitis and will be described hereinafter with reference to this application. However, it will be appreciated that the invention is not limited to this particular field of use.

The following description and drawings set forth certain illustrative aspects and implementations. These are indicative of but a few of the various ways in which one or more aspects may be employed. Other aspects, advantages, or novel features of the disclosure will become apparent from the following detailed description when considered in conjunction with the drawings.

BRIEF DESCRIPTION OF THE DRAWINGS

The accompanying drawings, which are incorporated in and constitute a part of the specification, illustrate various systems, methods, and other embodiments of the disclosure. Illustrated element boundaries (e.g., boxes, groups of boxes, or other shapes) in the figures represent one example of the boundaries. In some examples one element may be designed as multiple elements or multiple elements may be designed as one element. In some examples, an element shown as an internal component of another element may be implemented as an external component and vice versa. The patent or application file contains at least one drawing executed in color. Copies of this patent or patent application with color drawing(s) will be provided by the Office upon request and payment of the necessary fee.

DETAILED DESCRIPTION

Figures 1A, 1B, 1C:
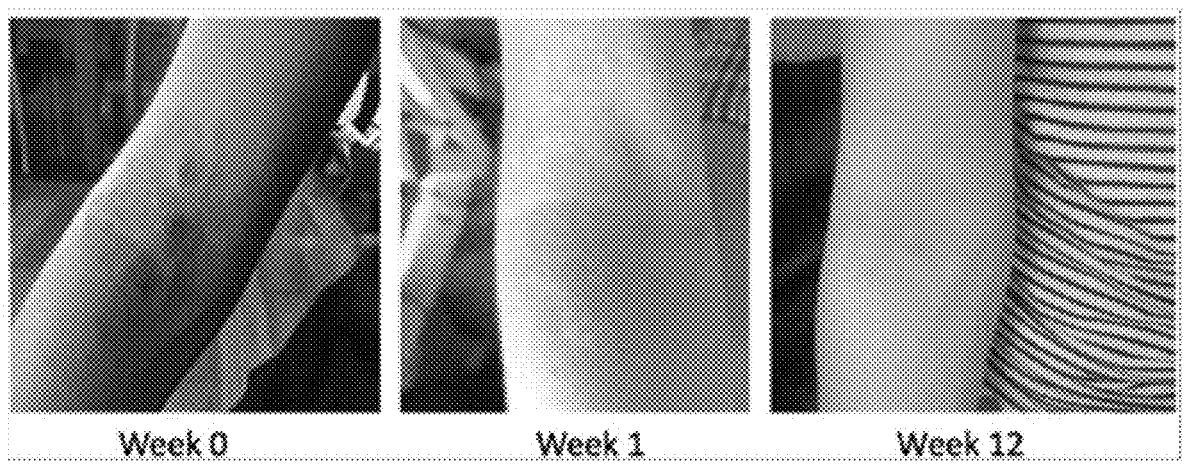
FIG. 1A illustrates one embodiment of chronological results of an arm associated with a dietary supplement composition as a prophylactic and treatment for skin diseases such as eczema and psoriasis and the like and method of treatment.
FIG. 1B illustrates one embodiment of chronological results of an arm associated with a dietary supplement composition as a prophylactic and treatment for skin diseases such as eczema and psoriasis and the like and method of treatment.
FIG. 1C illustrates one embodiment of chronological results of an arm associated with a dietary supplement composition as a prophylactic and treatment for skin diseases such as eczema and psoriasis and the like and method of treatment.

Embodiments or examples illustrated in the drawings are disclosed below using specific language. It will nevertheless be understood that the embodiments or examples are not intended to be limiting. Any alterations and modifications in the disclosed embodiments and any further applications of the principles disclosed in this document are contemplated as would normally occur to one of ordinary skill in the pertinent art. Described herein are examples of systems, methods, and other embodiments associated with automated secondary linking for fraud detection systems.

According to a first aspect of the present invention, there is provided a dietary supplement composition for at least treating an atopic or non-atopic disorder in a patient, the dietary supplement composition comprising as an active ingredient, an effective amount of: at least one nutrient being effective in enhancing phase II detoxification of the liver of the patient.

As will become apparent from the description below, the supplement composition described herein, (as noted in the below mentioned clinical trials) is effective in substantially correcting nutritional deficiencies associated with eczema, psoriasis, dermatitis or similar atopic or non-atopic conditions. Indeed the dietary supplement composition shows statistically significantly reduction in eczema symptoms of patients and/or complete remission of eczema symptoms substantially with no side-effects, and long-term use and safety being achieved.

Preferably, the at least one nutrient is effective for promoting the glycination pathway. Preferably, the at least one nutrient is glycine. The glycine may be provided in the form of L-glycine, protein powder, or any combination thereof. As such, in one embodiment, the dietary supplement may be provided in two forms, one containing glycine and the other a combination of glycine and vegetable protein.

Advantageously, the inclusion of glycine in the dietary supplement composition encourages phase 2 liver detoxification of salicylates in the patient, thereby enabling patients suffering from eczema to eat a wider variety of foods without adverse effect.

In a related aspect there is disclosed a dietary supplement composition as a prophylactic and treatment for skin diseases such as eczema and psoriasis and the like, the composition comprising: a phase II liver detoxification component having: glycine, and magnesium. In one embodiment, the glycine and magnesium are present in the supplement composition in a ratio of between about 20:1 and 20:8.

Preferably, the at least one nutrient is selected from the group comprising: glycine, vitamin B6, taurine, magnesium, or any combination thereof.

Advantageously, the inclusion of glycine, vitamin B6, the taurine, and the magnesium in the dietary supplement composition encourages phase 2 liver detoxification of salicylates in the patient, thereby enabling patients suffering from eczema to eat a wider variety of foods without adverse effect.

Preferably, the dietary supplement composition is substantially free of retinol. Preferably, the dietary supplement comprises beta-carotene (provitamin A) for the reason that retinol may dry out the skin whereas beta-carotene does not. Rather, beta-carotene increases in hydration.

Advantageously, the dietary supplement composition being substantially free of retinol, reduces the likelihood of the skin drying effect associated with vitamin A that causes a reduction in the production of sebum in the sebaceous glands, occurring in the patient.

The dietary supplement composition can further include at least one nutrient selected from the group comprising vitamin B1, vitamin B2, vitamin B3, vitamin B6, vitamin B7, vitamin B12, vitamin C, vitamin D, vitamin E, or any combination thereof. In one embodiment the nutrient or combination of nutrients is present in a ratio range of nutrient to liver detoxification component of between about 1:12 to about 1:17. The dietary supplement composition can further comprise calcium or a nutritionally acceptable salt present in a ratio of phase II liver detoxification component to calcium ranging from between about 10:7 to about 10:180.

The dietary supplement composition can further comprise Zinc in a trace amount effective for enhancing a wound healing function.

The dietary supplement composition can further comprise an effective amount of vitamin E for substantially inhibiting lipoxygenase formation, which is known to reduce the pathogenesis of dermatitis or eczema.

In a further related aspect there is disclosed a dietary supplement composition as a prophylactic and treatment for skin diseases such as eczema and psoriasis and the like comprising: a phase II liver detoxification component having: glycine, and magnesium. In one embodiment, the glycine and magnesium are present in the supplement composition in a ratio of between about 20:1 and 20:8. In this or another embodiment, at least one nutrient selected from the group comprising vitamin B1, vitamin B2, vitamin B3, vitamin B6, vitamin B7, vitamin B12, vitamin C, vitamin D, vitamin E, molybdenum, or any combination thereof. In this or another embodiment the nutrient or combination of nutrients is present in a ratio range of nutrient to liver detoxification component of between about 1:12 to about 1:17. The dietary supplement composition as a prophylactic and treatment for skin diseases such as eczema and psoriasis and the like may further comprise calcium or nutritionally acceptable salt present in a ratio of phase II liver detoxification component to calcium ranging from between about 10:7 to about 10:180. Zinc may also be present in an effective amount for enhancing a wound healing function. The dietary supplement composition as a prophylactic and treatment for skin diseases such as eczema and psoriasis and the like may further comprise an effective amount of vitamin E for substantially inhibiting lipoxygenase formation. The composition is taken as a food supplement and is effective in treatment of skin diseases, and substantially reducing the onset of skin disease.

Preferably, the dietary supplement composition further comprises chromium or nutritionally acceptable salt as an active ingredient in an effective amount to substantially modify a patient's inflammatory response by promoting conversion of DGLA to series 1 prostaglandin (PGE1). It has been found that chromium in the composition shows effectiveness for reducing blood sugar levels. [note: chromium does not promote PGE1—by preventing high blood sugar and the resulting high insulin response, chromium helps to prevent PGE1 blockage as high insulin blocks PGE1].

In one embodiment there is disclosed a prophylactic and treatment for skin diseases such as eczema and psoriasis and the like, comprising: a first dietary supplement composition comprising: a phase II liver detoxification component having: glycine, and magnesium. The glycine and magnesium are present in the supplement composition in a ratio of between about 20:1 and 20:8. In one embodiment, at least one nutrient selected from the group comprising vitamin B1, vitamin B2, vitamin B3, vitamin B6, vitamin B7, vitamin B12, vitamin C, vitamin D, vitamin E, molybdenum, or any combination thereof. In one embodiment, the nutrient or combination of nutrients is present in a ratio range of nutrient to liver detoxification component of between about 1:12 to about 1:17.

The prophylactic and treatment for skin diseases such as eczema and psoriasis and the like, may further comprise a second dietary supplement composition complementary to the first composition. In one embodiment, the second dietary supplement comprises calcium, magnesium and vitamin D3, wherein calcium and magnesium are present in the supplement composition in a ratio of between about 5:1 and 9:1. In one embodiment, the vitamin D3 is present in an effective amount to improve absorption of calcium. In one embodiment, the first and second dietary supplement compositions are administered spaced apart so as to substantially improve absorption of elements including zinc, and glycine. In one embodiment, the first and second dietary supplement compositions form a two-part treatment regimen for effectively treating skin diseases such as eczema and psoriasis. By separating the calcium component from the first dietary composition, there is greater overall absorption of nutrient substantially without interference of nutrient absorption by calcium. This two-part dosage regimen is shown to significantly reduce symptoms of eczema and psoriasis, and can thereafter be used as a prophylactic treatment.

In a further related aspect there is disclosed a method of treatment and prophylaxis for skin diseases such as eczema and psoriasis and the like comprising providing a dietary supplement composition in an ingestible or oral dosage form. In one embodiment, the dietary supplement composition comprising at least a phase II liver detoxification component having glycine and magnesium. In one embodiment, the glycine and the magnesium are present in the supplement composition in a ratio of between about 20:1 and 20:8. The method further includes metering a predetermined dosage amount. The method also includes applying the metered dose to liquid or food for consumption. The method includes repeating dosing regimen at least twice daily for a period of time effective for substantially reducing symptoms of the skin disease.

As discussed above, the composition used in the method of treatment can comprise at least a phase II liver detoxification component having glycine and magnesium. The glycine and the magnesium are present in the supplement composition in a ratio of between about 20:1 and 20:8. In one embodiment, at least one nutrient selected from the group comprising vitamin B1, vitamin B2, vitamin B3, vitamin B6, vitamin B7, vitamin B12, vitamin C, vitamin D, vitamin E, molybdenum, or any combination thereof. In one embodiment, the nutrient or combination of nutrients is present in a ratio range of nutrient to liver detoxification component of between about 1:12 to about 1:17. The supplement composition may further include calcium or nutritionally acceptable salt present in a ratio of phase II liver detoxification component to calcium ranging from between about 10:7 to about 10:180. In another embodiment, the supplement composition may further include an effective amount for enhancing a wound healing function and an effective amount of vitamin E for substantially inhibiting lipoxygenase formation.

The dietary supplement composition as a prophylactic and treatment for skin diseases such as eczema and psoriasis and the like can be formulated for administering to the patient orally. The composition can be administered at a dosage of about 0.1 g to about 25 g per day, and the dosage form can be provided in a range of forms selected from the group comprising: gels, liquids, syrups, powders, tablets, capsules, gummies, and granules.

In a further related aspect there is disclosed a dietary supplement composition as a prophylactic and treatment for skin diseases such as eczema and psoriasis and the like, the composition comprising a phase II liver detoxification component having glycine in an amount of about 60-80 mg, and magnesium in an amount of about 30 mg. The dietary supplement composition nutrients including a combination of Vitamin B1 (1.1 mg), Vitamin B2 (1.1 mg), Vitamin B3 (5 mg), Pyridoxine (2 mg), Biotin (vitamin B7) (15 micrograms), Vitamin B12 (cyanocobalamin) (5 micrograms), Vitamin D3 (5 micrograms), and molybdenum in an amount of about 45 micrograms, wherein the nutrient or combination of nutrients is present in a ratio range of nutrient to liver detoxification component of between about 1:12 to about 1:17; calcium (as calcium ascorbate) present in an amount of about 25 mg; Vitamin E (d-alpha tocopheryl succinate) present in an amount of about 10 mg; Zinc (zinc picolinate) present in an amount of about 2 mg; Chromium (chromium picolinate) present in an amount of about 25 micrograms; and fillers including flavouring agents and coloring agents and excipients.

In a related aspect of the present invention there is disclosed a dietary supplement composition as a prophylactic and treatment for skin diseases such as eczema, psoriasis, dermatitis and the like comprising: a phase II liver detoxification component including at least a combination of an amino acid such as glycine and magnesium are present in the supplement composition in a ratio of between about 20:1 and 20:8, wherein glycine and magnesium are present in the supplement composition in a ratio of between about 20:1 and 20:8. In one embodiment, at least one nutrient selected from the group comprising vitamin B1, vitamin B2, vitamin B3, vitamin B6, vitamin B7, vitamin B12, vitamin C, vitamin D, vitamin E, molybdenum, or any combination thereof, wherein the nutrient or combination of nutrients is present in a ratio range of nutrient to liver detoxification component of between about 1:12 to about 1:17. In one embodiment, a calcium in an amount of between about 60 mg to about 2000 mg; vitamin E in an amount ranging between about 1 mg to about 150 mg. In one embodiment, the dietary supplement includes zinc present in an amount ranging between about 0.1 mg and about 15 mg; and excipients for aiding formulation of the dietary supplement composition in solid, or liquid dosage forms.

In a related aspect there is disclosed a dietary supplement composition as a prophylactic and treatment for skin diseases such as eczema and psoriasis and the like, the composition comprising: a component selected from a group of nutrients being effective in enhancing phase II detoxification of the liver of the patient, wherein the component is present in a majority amount of the composition, and includes a composition comprising: about 400 mg to 1200 mg of glycine, about 60 mg to at least 250 mg of Magnesium or nutritionally effective salt, and at least one nutrient effective for promoting a wound healing effect in vivo. In one embodiment, the at least one nutrient includes zinc as a nutritionally effective salt present in an amount of about 4 mg to 14 mg. In one embodiment, the at least one nutrient effective for substantially inhibiting lipoxygenase formation wherein the at least one nutrient includes vitamin E in an amount of about 20 mg. In one embodiment, the at least one nutrient effective for reducing histamine levels in the patient wherein the at least one nutrient includes vitamin C in an amount of about 50 mg to 160 mg.

The dietary supplement composition can further comprise about 400 mg to 1100 mg of calcium; and an effective amount of at least one nutrient selected from the group of vitamins comprising of about 0.1 mg to about 10 mg vitamin B1, about 0.1 mg to about 6 mg, vitamin B2, about 1 mg to about 30 mg vitamin B3, about 0.1 mg to about 90 mg vitamin B6, about 1 mg to about 1200 mg vitamin E, about 1 µg to about 1200 µg vitamin B7, about 1 µg to about 600 µg vitamin B12, about 0.1 µg to about 100 µg vitamin D, and about 45 micrograms of molybdenum.

In a further related aspect there is disclosed prophylactic and treatment for skin diseases such as eczema and psoriasis and the like, comprising: a first dietary supplement composition comprising a phase II liver detoxification component having glycine in an amount of 800 mg, and magnesium in an amount of 120 mg, nutrients including vitamin B1 in an amount of 1.2 mg, vitamin B2 in an amount of 1.2 mg, vitamin B3 in an amount of 2 mg, vitamin B6 in an amount of 2 mg, vitamin B7 in an amount of 0.03 mg, vitamin B12 in an amount of 0.01 mg, vitamin C as magnesium ascorbate in an amount of 60 mg; Zinc (zinc picolinate) present in an amount of 8 mg; Molybdenum present in an amount of about 0.045 mg; and fillers.

A second dietary supplement composition complementary to the first composition comprising calcium present in an amount of about 1100 mg; magnesium present in an amount of 120 mg; and vitamin D3 present in an amount of about 0.02 mg. In one embodiment, the first and second dietary supplement compositions are administered spaced apart so as to substantially improve absorption of elements including zinc, and glycine.

In yet a further related aspect there is disclosed prophylactic and treatment for skin diseases such as eczema and psoriasis and the like, comprising: a phase II liver detoxification component having: Glycine present in an amount of about 60-80 mg; and magnesium pre present in an amount of about 30 mg; at least one nutrient effective for substantially inhibiting lipoxygenase formation wherein the at least one nutrient includes vitamin E in an amount of about 10 mg; nutrients including vitamin B1 in an amount of 1.1 mg, vitamin B2 in an amount of 1.1 mg, vitamin B3 in an amount of 5 mg, vitamin B6 in an amount of 2 mg, vitamin B7 in an amount of 0.015 mg, vitamin B12 in an amount of 0.005 mg, vitamin C as magnesium ascorbate in an amount of 25 mg, molybdenum present in an amount of about 0.045 mg; and vitamin D3 in an amount of 0.005 mg; chromium present in an amount of about 0.025 mg to substantially modify a patient's inflammatory response by promoting conversion of DGLA to series 1 prostaglandin (PGE1); zinc present in an amount of about 2 mg for enhancing a wound healing function; and fillers.

Lipdxygenase Inhibition

Preferably, the dietary supplement composition further comprises as an active ingredient, an effective amount of at least one nutrient being effective for inhibiting lipoxygenase formation in the patient. Preferably, the at least one nutrient is vitamin E. Advantageously, the inclusion of vitamin E in the dietary supplement composition inhibits lipoxygenase formation which is known to reduce the pathogenesis of dermatitis or eczema.

Wound Healing

Preferably, the dietary supplement composition further comprises as an active ingredient an effective amount of at least one nutrient being effective for promoting a wound healing effect in vivo. Preferably, the at least one nutrient is selected from the group comprising: coenzyme Q10, and zinc, or any combination thereof. Advantageously, the inclusion of coenzyme Q10 in the dietary supplement composition encourages wound healing. Advantageously, the inclusion of zinc in the dietary supplement composition aids cell and tissue growth, and promotes the conversion of omega-6 (linoleic acid) into gamma-linolenic acid (GLA) thereby reducing the onset of such skin disorders as dermatitis and eczema. Advantageously, the inclusion of zinc in the dietary supplement composition encourages wound healing.

Recycling Vitamin E

Preferably, the dietary supplement composition further comprises as an active ingredient an effective amount of at least one nutrient being effective for recycling vitamin E in the patient. Preferably, the at least one nutrient is vitamin C. Advantageously, the inclusion of vitamin C in the dietary supplement composition encourages the recycling of vitamin E within the patient to help lower serum immunoglobulin E (IgE) concentrations within the blood of patients suffering from such skin disorders as eczema, thereby resulting in a lower frequency of allergen sensitization associated with such disorders.

Reduce Histamine Level

Preferably, the dietary supplement composition further comprises as an active ingredient, an effective amount of at least one nutrient being effective for reducing the level of histamine in the patient. Preferably, the at least one nutrient is a vitamin selected from the group of vitamins comprising: vitamin C, vitamin B6, or any combination thereof.

Advantageously, the inclusion of vitamin B6 in the dietary supplement composition helps to prevent the release of histamine within the body, which is known to cause allergic inflammation in patients.

Minerals

Preferably, the dietary supplement composition further comprises as an active ingredient, an effective amount of at least one mineral. Preferably, the at least one mineral is a polyvalent metal. Preferably, the polyvalent metal is selected from the group comprising: copper, chromium, magnesium, manganese, molybdenum, zinc, calcium, or any nutritionally acceptable salt 10 thereof.

Advantageously, the inclusion of copper in the dietary supplement composition helps to stimulate the immune system to fight infections, to repair injured tissues, and to promote healing.

Advantageously, the inclusion of copper in the dietary supplement composition helps to 15 neutralize free-radicals formed within the body due to oxidative stress, which can cause severe damage to cells.

Advantageously, the inclusion of chromium in the dietary supplement composition helps to reduce the need for high insulin levels needed within the body of patients suffering from such disorders as dermatitis or eczema, thereby promoting the conversion of dihomo gamma-linolenic acid (DGLA) to series 1 prostaglandins (PGE1), which has the effect of reducing the inflammation associated with such disorders.

Advantageously, the inclusion of chromium in the dietary supplement composition assists in the breakdown of proteins, carbohydrates, and fats within the body.

Advantageously, the inclusion of magnesium in the dietary supplement composition when combined with glycine, vitamin B6, and taurine, encourages phase 2 liver detoxification of salicylates in the patient, thereby enabling patients suffering from such skin disorders as eczema, to eat a wider variety of foods without adverse effect. Advantageously, the inclusion of manganese in the dietary supplement composition supplies manganese for the formation of connective tissues and collagen which provides strength and resilience within the skin of sufferers of eczema and atopic and/or non-atopic patients.

Advantageously, the inclusion of molybdenum in the dietary supplement composition helps to replenish the balance of this mineral within the body of patients suffering from such skin disorders as dermatitis or eczema. Advantageously, the inclusion of molybdenum or any nutritionally acceptable salt thereof in the dietary supplement composition acts against sulphites (such as food preservatives), to which many patients suffering from skin disorders such as dermatitis or eczema, express sensitivity towards.

Advantageously, the inclusion of zinc in the dietary supplement composition aids cell and tissue growth, and promotes the conversion of omega-6 (linoleic acid) into gamma-linoleic acid (GLA), thereby reducing the onset of such skin disorders as dermatitis and eczema. Advantageously, the inclusion of zinc in the dietary supplement composition encourages wound healing. Advantageously, the inclusion of calcium in the dietary supplement composition encourages thickening of the epidermis to trap moisture and promote lipid production, thus providing strength and skin hydration for sufferers of eczema and atopic and/or non-atopic patients. Preferably, the copper is selected from the group comprising: cupric oxide, copper gluconate, or any combination thereof.

Preferably, the chromium is selected from the group comprising: chromium amino acid chelate, chromium picolinate, chromium chloride, chromium nicotinate, high-chromium yeast, chromium citrate, or any combination thereof. Preferably, the magnesium is selected from the group comprising: magnesium oxide, magnesium phosphate, magnesium glycinate, or any combination thereof. Preferably, the manganese is selected from the group comprising: manganese amino acid chelate, manganese gluconate, manganese sulfate, or any combination thereof.

Preferably, the molybdenum is selected from the group comprising: elemental molybdenum, sodium molybdate, ammonium molybdate, or any combination thereof. Preferably, the zinc is provided in the form of zinc oxide, zinc gluconate, zinc picolinate, or any combination thereof. Preferably, the calcium is provided in the form of calcium citrate, calcium carbonate, hydroxyapatite, or any combination thereof.

Vitamins

Preferably, the dietary supplement composition further comprises as an active ingredient, an effective amount of at least one vitamin. Advantageously, the at least one vitamin in the dietary supplement composition imparts the antioxidant and/or anti-inflammatory properties of the at least one vitamin on the body of patients suffering from such skin disorders as dermatitis and eczema, to help alleviate the symptoms associated with such disorders. Preferably, the at least one vitamin is selected from the group of vitamins comprising: vitamin B1, vitamin B2, vitamin B3, vitamin B5, vitamin B6, vitamin B7, vitamin B9, vitamin B12, vitamin C, vitamin D, vitamin E, or any combination thereof.

Advantageously, the vitamin E in the dietary supplement composition acts as an antioxidant agent and helps to lower serum immunoglobulin E (IgE) concentrations within the blood of patients suffering from such skin disorders as eczema, thereby resulting in a lower frequency of allergen sensitisation associated with such disorders. Preferably, the vitamin B1 is provided in the form of thiamine or any nutritionally acceptable salt thereof.

Advantageously, the vitamin B1 in the form of thiamine or any nutritionally acceptable salt thereof in the dietary supplement composition, acts as an antioxidant agent and helps to scavenge and neutralize free radicals within the body, thereby reducing or even helping to prevent some of the adverse effects associated with free radicals in patients suffering from such disorders as dermatitis or eczema.

Advantageously, the vitamin B1 in the form of thiamine or any nutritionally acceptable salt thereof in the dietary supplement composition helps the body to metabolise fats.

Advantageously, the vitamin B1 in the form of thiamine or any nutritionally acceptable salt 25 thereof in the dietary supplement composition acts against sulphites (such as food preservatives), to which many patients suffering from skin disorders such as dermatitis or eczema, express sensitivity towards.

Preferably, the vitamin B2 is provided in the form of riboflavin or any nutritionally acceptable salt thereof. Advantageously, the vitamin B2 in the form of riboflavin in the dietary supplement composition helps to replenish the balance of this vitamin within the body of patients suffering from such disorders as dermatitis and eczema. Preferably, the vitamin B3 is provided in the form of niacin or any nutritionally acceptable salt thereof.

Advantageously, the vitamin B3 in the form of niacin in the dietary supplement composition helps to replenish the balance of this vitamin within the body of patients suffering from such disorders as dermatitis and eczema.

Advantageously, the vitamin B3 in the form of niacin in the dietary supplement composition has a synergistic effect when combined with vitamin C to enhance the absorption of chromium, which decreases the need for high insulin in the body of patients suffering from such disorders as dermatitis or eczema, thereby promoting the conversion of dihomo gamma-linolenic acid (DGLA) to series 1 prostaglandins (PGE1), which has the effect of reducing the inflammation associated with such disorders.

Preferably, the vitamin B5 is provided in the form of pantothenic acid or any nutritionally acceptable salt thereof. Advantageously, the vitamin B5 in the form of pantothenic acid or any nutritionally acceptable salt thereof in the dietary supplement composition, acts as an antioxidant agent helps to scavenge and neutralize free radicals within the body, thereby reducing or even helping to prevent some of the adverse effects associated with free radicals in patients suffering from such skin disorders as dermatitis or eczema. Advantageously, the vitamin B5 in the form of pantothenic acid or any nutritionally acceptable salt thereof in the dietary supplement composition has a synergistic effect when combined with vitamin C to promote wound healing.

Advantageously, the vitamin B5 in the form of pantothenic acid or any nutritionally acceptable salt thereof in the dietary supplement composition acts against sulphites (such as food preservatives), to which many patients suffering from skin disorders such as dermatitis or eczema, express sensitivity towards.

Preferably, the vitamin B6 is provided in the form of pyridoxine or any nutritionally acceptable salt thereof. Advantageously, the vitamin B6 in the form of pyridoxine in the dietary supplement composition when combined with glycine, taurine, and magnesium, encourages phase 2 liver detoxification of salicylates in the patient, thereby enabling patients suffering from eczema to eat a wider variety of foods without adverse effect. Advantageously, the vitamin B6 in the form of pyridoxine or any nutritionally acceptable salt thereof in the dietary supplement composition helps to prevent the release of histamine within the body of patients suffering from such skin disorders as dermatitis or eczema, which is known to cause allergic inflammation in patients.

Preferably, the vitamin B7 is provided in the form of biotin. Advantageously, the vitamin B7 in the form of biotin in the dietary supplement composition helps to prevent biotin deficiency which can cause dermatitis or eczema.

Preferably, the vitamin B9 is provided in the form of folic acid or any nutritionally acceptable salt thereof. Advantageously, the vitamin B9 in the form of folic acid in the dietary supplement composition helps to replenish the balance of this vitamin within the body of patients suffering from such disorders as dermatitis or eczema.

Preferably, the vitamin B12 is provided in the form of cyanocobalamin. Advantageously, the vitamin B12 in the form of cyanocobalamin in the dietary supplement composition helps to replenish the balance of this vitamin within the body of patients suffering from such disorders as dermatitis or eczema. Preferably, the vitamin C is provided in the form of magnesium ascorbate or any nutritionally acceptable salt thereof. Advantageously, the vitamin C in the dietary supplement composition can encourage the recycling of vitamin E within the patient to help lower serum immunoglobulin E (IgE) concentrations within the blood of patients suffering from such disorders as eczema, thereby resulting in a lower frequency of allergen sensitisation associated with such disorders.

Preferably, the vitamin D is provided in the form of cholecalciferol. Advantageously, the vitamin D in the form of cholecalciferol in the dietary supplement composition helps to replenish the balance of this vitamin within the body of patients suffering from such disorders as eczema. Preferably, the vitamin E is selected from the group comprising: a tocopherol, a tocotrienol, or any combination thereof. Advantageously, the vitamin E in the dietary supplement composition acts as an anti-inflammatory agent to inhibit lipoxygenase formation, which is known to reduce the pathogenesis of dermatitis or eczema.

Advantageously, the vitamin E in the dietary supplement composition acts as an anti-inflammatory agent to inhibit leukotriene B4 formation, which is known to prolong the inflammatory process associated with eczema.

Excipients

Preferably, the dietary supplement composition further comprises at least one excipient. Advantageously, the inclusion of excipients in the dietary supplement composition aids in the formulation of the dietary supplement composition in solid dosage form such as tablets. Preferably, the at least one excipient is a filler, coloring agent or binder selected from the group comprising: a saccharide, a protein, a polymer, calcium, rice flour, glycine, lysine, taurine, chlorella, beta-carotene, sodium bicarbonate, or any combination thereof. Preferably, the composition is formulated for administering to the patient orally. Advantageously, the dietary supplement composition can be orally ingested.

Preferably, the composition is in solid dosage form.

Advantageously, the dietary supplement composition can be orally ingested in solid form. Preferably, the composition is in liquid dosage form.

Advantageously, the dietary supplement composition can be orally ingested in liquid form.

According to a second aspect of the present invention, there is provided a method of at least treating an atopic or non-atopic disorder in a patient, the method comprising the step of: administering to the patient an effective daily dosage of a dietary supplement composition as described in any one of the preceding paragraphs. Preferably, the dietary supplement composition is formulated for administering to the patient orally.

Preferably, the dietary supplement composition is administered at a dosage of about 0.1 g to about 25 g per day.

Preferably, the dietary supplement composition is administered at a dosage of about 5 g to about 15 g per day.

5 Preferably, the dietary supplement composition is in dosage form selected from the group comprising: gels, liquids, syrups, powders, tablets, capsules, gummies, and granules.

According to a third aspect of the present invention, there is provided a use of a dietary supplement composition according to the preceding paragraphs for at least treating an atopic or non-atopic disorder in a patient.

10 According to a fourth aspect of the present invention, there is provided a dietary supplement composition as a prophylactic and treatment for skin diseases such as eczema and psoriasis and the like, the composition comprising as active ingredients in a daily dosage, an effective amount of: at least one nutrient selected from the group comprising: glycine, calcium, or any combination thereof.

Advantageously, the calcium in the dietary supplement composition promotes a healthy acid mantle, which protects the skin barrier from microbe invasion and infections, which is advantageous to eczema sufferers.

Preferably, the dietary supplement composition further comprises as active ingredients, an effective amount of at least one nutrient selected from the group comprising: vitamin C, coenzyme Q10, zinc, vitamin E, or any combination thereof.

Preferably, the dietary supplement composition further comprises as active ingredients, an effective amount of at least one nutrient selected from the group of vitamins comprising: vitamin B1, vitamin B2, vitamin B3, vitamin B6, vitamin B5, vitamin B7, vitamin B9, vitamin B12, vitamin D, or any combination thereof.

Preferably, the dietary supplement composition further comprises as active ingredients, an effective amount of at least one nutrient selected from the group of minerals comprising: elemental magnesium, elemental manganese, elemental calcium, elemental copper, elemental chromium, elemental molybdenum, elemental zinc, or any combination thereof.

Preferably, the dietary supplement composition further comprises fillers, coloring agents and binders including from the group comprising: taurine, beta-carotene, or any combination thereof. Advantageously, the taurine in the dietary supplement composition when combined with glycine, vitamin B6, and magnesium, encourages phase 2 liver detoxification of salicylates in the patient, thereby enabling patients suffering from such disorders as dermatitis or eczema, to eat a wider variety of foods without adverse effect. Preferably, the dietary supplement composition is substantially free of retinol. Advantageously, the dietary supplement composition being substantially free of retinol reduces the likelihood of the skin drying effect associated with this form of vitamin A that causes a reduction in the production of sebum in the sebaceous glands, occurring in the patient.

Preferably, the composition is in solid dosage form. Advantageously, the dietary supplement composition can be orally ingested in solid form. Preferably, the composition is in liquid dosage form. Advantageously, the dietary supplement composition can be orally ingested in liquid form.

According to a fifth aspect of the present invention, there is provided a dietary supplement composition as a prophylactic and treatment for skin diseases such as eczema and psoriasis and the like, the composition comprising as active ingredients in a daily dosage, an effective amount of: at least one nutrient selected from the group comprising: about 5 mg to about 7000 mg glycine, about 1 mg to about 3000 mg calcium, or any combination thereof.

Preferably, the dietary supplement composition further comprises as active ingredients, an effective amount of at least one nutrient selected from the group comprising: about 5 mg to about 2000 mg vitamin C, about 1 mg to about 1200 mg vitamin E, 3 mg to about 1500 mg coenzyme Q10 (and/or about 0.1 mg to about 90 mg elemental zinc), or any combination thereof.

Preferably, the dietary supplement composition further comprises as active ingredients, about 0.1 mg to about 10 mg vitamin B1, about 0.1 mg to about 6 mg vitamin B2, about 1 mg to about 30 mg vitamin B3, about 0.1 mg to about 90 mg vitamin B6, about 0.1 mg to about 20 mg vitamin B5, about 1 µg to about 1200 µg vitamin B7, about 1 µg to about 600 µg vitamin B9, about 1 µg to about 600 µg vitamin B12, about 0.1 µg to about 100 µg vitamin D, or any combination thereof.

Preferably, the dietary supplement composition further comprises as active ingredients, an effective amount of at least one nutrient selected from the group of minerals comprising of about 5 mg to about 600 mg elemental magnesium, about 0.1 mg to about 10 mg elemental manganese, about 0.01 mg to about 15 mg elemental copper, about 1 µg to about 800 µg elemental chromium, about 2 µg to about 2000 µg elemental molybdenum, about 0.1 mg to about 30 mg elemental zinc, or any combination thereof.

Preferably, the dietary supplement composition further comprises as fillers an amount of about 1 mg to about 2000 mg taurine, about 1 µg to about 2000 µg beta-carotene, or any combination thereof. Preferably, the dietary supplement composition is substantially free of retinol. Advantageously, the dietary supplement composition being substantially free of retinol reduces the likelihood of the skin drying effect associated with vitamin A that causes a reduction in the production of sebum in the sebaceous glands, occurring in the patient.

In one embodiment, the composition is in solid dosage form. In another embodiment, the composition is in liquid dosage form.

According to a sixth aspect of the present invention, there is provided a method for preparing a dietary supplement composition for at least treating an atopic or non-atopic disorder in a patient, the method comprising the steps of: providing as active ingredients, an effective amount of at least one nutrient selected from the group comprising: glycine, calcium, or any combination thereof; and combining the at least one nutrient with at least one excipient into a suitable dosage form.

Advantageously, the dietary supplement composition can be formulated for oral ingestion by combining the active ingredients with at least one excipient.

Preferably, the method further comprises the step of: providing as active ingredients, an effective amount of at least one nutrient selected from the group comprising: vitamin C, coenzyme Q10, and/or zinc, vitamin E, or any combination thereof.

Preferably, the method further comprises the step of: providing as active ingredients, an effective amount of at least one vitamin selected from the group of vitamins comprising: vitamin B1, vitamin B2, vitamin B3, vitamin B6, vitamin B5, vitamin B7, vitamin B9, vitamin B12, vitamin D, or any combination thereof.

Preferably, the method further comprises the step of: providing as active ingredients, an effective amount of at least one mineral selected from the group of minerals comprising: elemental magnesium, elemental copper, elemental chromium, elemental molybdenum, elemental zinc, or any combination thereof.

Preferably, the method further comprises the step of providing as active ingredients, an effective amount of taurine, beta-carotene, or any combination thereof.

Preferably, the dietary supplement composition is substantially free of retinol.

Advantageously, the dietary supplement composition being substantially free of retinol reduces the likelihood of the skin drying effect associated with vitamin A that causes a reduction in the production of sebum in the sebaceous glands, occurring in the patient.

Preferably, the at least one excipient is a filler, coloring agent or a binder selected from the group comprising: a saccharide, a protein, a polymer, calcium, magnesium, protein powder, glycine, lysine, taurine, chlorella, beta-carotene, sodium bicarbonate, rice flour, or any combination thereof.

Preferably, the dietary supplement composition is formulated for administering to the patient orally.

Advantageously, the dietary supplement composition can be orally ingested.

Preferably, the dietary supplement composition is administered at a dosage of about 0.1 g to about 25 g per day.

Preferably, the dietary supplement composition is administered at a dosage of about 5 g to about 15 g per day.

Preferably, the dosage form is selected from the group comprising: gels, liquids, syrups, powders, tablets, capsules, gummies, and granules.

Advantageously, the dietary supplement composition can be orally ingested in a solid, semisolid, or liquid form.

According to a seventh aspect of the present invention, there is provided a dietary supplement composition, comprising an effective amount of the following active ingredients: glycine, calcium, vitamin C, and vitamin E, wherein the dietary supplement composition is substantially free of retinol.

Preferably, the dietary supplement composition further comprises an effective amount of the following active ingredients: at least one vitamin selected from the group comprising: vitamin B1, vitamin B2, vitamin B3, vitamin B6, vitamin B5, vitamin B7, vitamin B9, vitamin B12, and vitamin D.

Preferably, the dietary supplement composition further comprises an effective amount of the following active ingredients: at least one mineral selected from the group comprising: elemental magnesium, elemental manganese, elemental copper, elemental chromium, elemental molybdenum, and elemental zinc.

Preferably, the dietary supplement composition further comprises an effective amount of the following active ingredients: at least one nutrient selected from the group comprising: taurine and beta-carotene.

Preferably, the composition is in solid dosage form.

Preferably, the composition is in liquid dosage form.

Other aspects of the invention are also disclosed.

Notwithstanding any other forms which may fall within the scope of the present invention, preferred embodiments of the invention will now be described, by way of reference to the accompanying examples only.

Before describing the present invention in detail, it is to be understood that the preferred embodiments of this invention are not limited to particular active ingredients, as such may vary. It is also to be understood that the terminology used herein is for the purpose of describing particular embodiments only, and is not intended to be limiting.

One embodiment of the present invention pertains to a dietary supplement composition that is suitably formulated for treating an atopic or non-atopic disorder in a patient suffering from such skin disorders including eczema, and psoriasis, to supplement their diet with the right balance of nutrients to suppress the inflammation associated with such disorders, as well as to stimulate collagen synthesis, improve the skin's texture, help with proper essential fatty acid metabolism, and generally protect the skin from free radical damage. Continued use of the dietary supplement composition in a majority of patients has been shown to significantly improve eczema and psoriasis and in a significant number of cases a complete remission of eczema and psoriasis symptoms is achieved.

The dietary supplement composition is also formulated to provide support to patients who are suffering from other health conditions, including, eczema, psoriasis, dermatitis, hives, a fatty liver, hay fever, chemical sensitivities, and other skin disorders, where the patient's condition can be assisted, alleviated or treated with the elected nutrients in the dietary supplement composition. The dietary supplement composition may also be beneficial as a general health and wellbeing formula.

The dietary supplement composition according to preferred embodiments of the present invention is formulated with active ingredients as follows. It is important to note that the dietary supplement composition is not meant as a replacement of those ingredients naturally produced in the body and/or consumed in the diet, but rather represent a dietary supplement composition to increase normal levels of the above ingredients in the body.

In the body, oxidation reactions can produce free radicals, namely, reactive molecular species 30 with unpaired electrons that oxidize other molecules to gain electrons and stabilize themselves. The reaction starts a chain reaction to produce another free radical, initiating a macromolecules, such as DNA, proteins, carbohydrates, and lipids causing irreparable damage. Free radical damage can also cause unsaturated bonds in membrane lipids to lose fluidity when peroxidized and proteins to denature. The oxidative damage created by free radicals, referred to as oxidative stress, has been associated with certain disorders that result in inflammation, in particular, dermatitis or eczema.

In preferred embodiments, the dietary supplement composition comprises an effective amount of certain nutrients that have antioxidant properties, which are capable of slowing or preventing the oxidation of other molecules within the patient so as to help to reduce the symptoms of irritated skin and ease the discomfort caused by such skin disorders.

In preferred embodiments, the nutrients are selected from the group comprising: vitamins such as vitamin C and vitamin E, and any combination thereof.

Vitamin C or L-ascorbic acid is an essential nutrient for humans and certain other animal species. As an antioxidant agent, vitamin C protects cells against damage by free radicals, which are by-products of normal cell activity that participate in chemical reactions, some of which can be harmful.

In this embodiment, the inclusion of vitamin C in the dietary supplement composition as an antioxidant agent helps to prevent the release of histamine within the body, which is known to cause allergic inflammation in patients. The ascorbate ion also acts as an antioxidant by protecting the body against oxidative stress.

In a preferred embodiment, the vitamin C is provided as a nutrient in the form of magnesium ascorbate.

Unexpected good results have been obtained using magnesium ascorbate in the composition in the range of between about 5 mg to about 2000 mg, more preferably, in the range of between about 10 mg to about 500 mg, and optimally in the range of between about 20 mg to about 200 mg.

In other embodiments, the vitamin C may be provided in other forms including, but not limited to: ascorbic acid, sodium ascorbate, calcium ascorbate, potassium ascorbate, or fatty acid esters of ascorbic acid: ascorbyl palmitate, or ascorbyl stearate.

Vitamin E refers to a group of eight fat-soluble compounds that include both tocopherols and tocotrienols. One of the many different forms of vitamin E, α-tocopherol, is the most biologically active form of vitamin E, and can be found most abundantly in wheat germ oil, sunflower, and safflower oils. α-Tocopherol is a fat-soluble antioxidant agent that stops the production of reactive oxygen species formed when fat undergoes oxidation, thereby protecting cell membranes within the body.

In this embodiment, the oxidized α-tocopheroxyl radicals produced in this process may be recycled back to the active reduced form through reduction by other antioxidant agents, such as, for example, the synergistic effect of a combination of ascorbate ions, thereby enabling α-tocopherol to circulate around the body for longer. As a benefit, the recycling of vitamin E within the body helps to lower serum immunoglobulin E (IgE) concentrations within the blood of patients suffering from such disorders as eczema, thereby resulting in a lower frequency of allergen sensitisation associated with such disorders.

The inclusion of vitamin E as an anti-inflammatory agent in the dietary supplement composition has been found to inhibit lipoxygenase formation, which is known to reduce the pathogenesis of eczema. It has also been found that vitamin E inhibits leukotriene B4 formation which is known to prolong the inflammatory process associated with eczema.

In a preferred embodiment, the vitamin E used in the dietary supplement composition is provided as α-tocopherol in the form of d-alpha tocopheryl succinate.

Good results have been obtained using d-alpha tocopheryl succinate in the composition in the range of between about 1 mg to about 1200 mg, more preferably, in the range of between about 2 mg to about 500 mg, and optimally in the range of between about 4 mg to about 40 mg.

In other embodiments, the vitamin E may be provided in one of its other naturally or artificially occurring forms, or nutritionally acceptable salt thereof.

In a preferred embodiment, the dietary supplement composition comprises an effective amount of one or more nutrients having anti-inflammatory properties for reducing the inflammation caused by atopic and/or non-atopic disorders in patients. The nutrients used in the dietary supplement composition are selected from the following group of nutrients comprising: vitamin E, coenzyme Q10 (and or zinc), glycine, or any combination thereof.

It will be appreciated by skilled persons, that glycine, taurine and molybdenum are rarely used in multi-vitamin and mineral supplements.

In this embodiment, the inclusion of vitamin E as an anti-inflammatory agent in the dietary supplement composition has been found to inhibit lipoxygenase formation, which is known to reduce the pathogenesis of eczema. It has been found that vitamin E inhibits leukotriene B4 formation which is known to prolong the inflammatory process associated with eczema.

Coenzyme Q10 is an oil-soluble, vitamin-like nutrient, which is present in most eukaryotic cells, primarily in the mitochondria. Coenzyme Q10 may work synergistically with certain antioxidant agents to elevate cellular levels of vitamins C, E, and glutathione and to help regulate blood sugar and enhance insulin sensitivity.

In this embodiment, coenzyme Q10 is included in the dietary supplement composition to act as an anti-inflammatory agent to encourage wound healing. Skin concentrations of coenzyme Q10 markedly decline as you age so it is advantageous for adults to increase their intake of coenzyme Q10. As a safe dosage has not been set for children, coenzyme Q10 would preferably be in the adult embodiment and replaced with zinc, a wound healing mineral, in the children's composition.

Good results have been obtained using coenzyme Q10 in the composition in the range of between about 3 mg to about 1500 mg, more preferably, in the range of between about 5 mg to about 500 mg, and optimally in the range of between about 10 mg to about 50 mg.

Glycine is an amino acid, which is used by the body as a building block for making proteins, peptides, purines, nucleic acids and other amino acids. Glycine is also used for promoting growth-hormone release. Most proteins incorporate only small quantities of glycine, a notable exception being collagen, in which more than one-third of the collagen in skin comprises glycine.

In this embodiment, the inclusion of glycine in the dietary supplement composition, in combination with vitamin B6, taurine, and magnesium, has been found to encourage phase 2 liver detoxification of salicylates in the patient, thereby enabling patients suffering from skin diseases such as eczema and psoriasis to eat a wider variety of foods without adverse effect.

Unexpected good results have been obtained using glycine in the composition in the range of between about 5 mg to about 7000 mg, more preferably, in the range of between about 10 mg to about 1500 mg, and optimally in the range of between about 100 mg to about 1200 mg.

In other embodiments, glycine may be provided in the form of gelatin or protein powders which are rich sources of this particular nutrient.

Vitamins that are not beneficial for atopic eczema and other dry skin conditions include retinol, which is known to reduce the production of sebum in the sebaceous glands thus having a 'skin drying' effect. Many commercially available multi-vitamin and mineral supplements contain retinol/vitamin A, thereby rendering these supplements counterproductive for eczema and other dry skin conditions.

In preferred embodiments, the dietary supplement composition is substantially free of retinol, thereby reducing the likelihood of the skin drying effect associated with vitamin A occurring in patients suffering from such skin disorders as dermatitis or eczema.

In other embodiments, a small amount of vitamin A, in the form of beta-carotene, may be used in the dietary supplement composition to help replenish the balance of this vitamin within the body of patients so as to reduce the likelihood of other problems occurring due to vitamin A deficiency, most notably, night blindness. Beta-carotene, a dietary source of provitamin A, does not reduce lipid production within the skin so it does not pose the same problem as retinol, making it ideal for sufferers of eczema and other dry skin disorders.

Many of the vitamins and minerals recommended for healthy skin, which are present in most multi-vitamin and mineral supplements, are known to compete with each other for absorption and can affect the absorption of certain minerals such as zinc and copper—two of the most important nutrients necessary for collagen production and normal skin function.

In preferred embodiments, the dietary supplement composition comprises a balanced amount of vitamins and minerals divided into two separate formulas and provided together, or provided as one product with a reduced dosage of calcium, to reduce competition between other active ingredients within the composition.

B vitamins are a group of eight water-soluble vitamins that play important roles in cell metabolism. The B vitamins were once thought to be a single vitamin, referred to as vitamin B. Later research showed that they are chemically distinct vitamins that often coexist in the same foods. In general, supplements containing all eight are referred to as a vitamin B complex. All B vitamins are water-soluble, and are dispersed throughout the body. Most of the B vitamins must be replenished regularly, since any excess is excreted in the urine.

Vitamin B1 assists in metabolizing carbohydrates and fats, and the generation of energy. It is a necessary vitamin for normal nerve functioning as well as many cellular processes. Vitamin B1 also acts against sulphites (such as food preservatives), to which many patients suffering from skin disorders such as psoriasis, dermatitis or eczema, express sensitivity towards.

In a preferred embodiment, the vitamin B1 used in the dietary supplement composition is thiamine provided in the form of thiamine hydrochloride, thiamine mononitrate, or any nutritionally acceptable salt thereof. It has been found that the inclusion of thiamine in the dietary supplement composition as an antioxidant agent helps to scavenge and neutralize free radicals within the body, thereby reducing or even helping to prevent some of the adverse effects associated with such free radicals in patients suffering from such disorders as dermatitis or eczema.

Good results have been obtained using thiamine hydrochloride in the range of between about 0.1 mg to about 10 mg in the composition.

Vitamin B2 is also known as riboflavin. Riboflavin plays a role in energy production and it is required for the conversion of vitamin B6 into pyridoxal 5'-phosphate. Vitamin B2 deficiency can cause dermatitis, scaly skin and cracked lips and corners of the mouth.

In a preferred embodiment, the vitamin B2 used in the dietary supplement composition is 20 riboflavin.

Good results have been obtained using riboflavin in the composition in the range of between about 0.1 mg to about 6 mg in the composition, more preferably, in the range of between about 0.2 mg to about 4 mg, and optimally in the range of between about 0.25 mg to about 3 mg.

Vitamin B3 is a water-soluble vitamin also known as niacin (nicotinic acid). Vitamin B3 helps the body produce energy by aiding the conversion of carbohydrates into glucose. It improves circulation and assists with the production of various sex and stress-related hormones. Vitamin B3 and vitamin C work synergistically to enhance the absorption of chromium, which decreases the need for high insulin in the body. Vitamin B3 deficiency causes pellagra; the symptoms include dermatitis, red skin lesions, sensitivity to sunlight, diarrhea and dementia.

In a preferred embodiment, the vitamin B3 used in the dietary supplement composition is provided in the form of niacin.

Good results have been obtained using niacin in the composition in the range of between about 1 mg to about 30 mg in the composition, more preferably, in the range of between about 2 mg to about 25 mg, and optimally in the range of between about 2 mg to about 10 mg.

Vitamin B5 is an important nutrient for the synthesisation and metabolization of fats, carbohydrates and proteins. A vitamin B5 deficiency may cause impaired energy production due to low coenzyme A levels, which could cause symptoms of irritability, fatigue, and apathy. Vitamin B5 also acts against sulphites (such as food preservatives), to which many patients suffering from skin disorders such as dermatitis or eczema, express sensitivity towards.

In this embodiment, the vitamin B5 has been included in the dietary supplement composition as an antioxidant agent to help to scavenge and neutralize free radicals within the body, thereby reducing or even helping to prevent some of the adverse effects associated with free radicals in patients suffering from such disorders as dermatitis or eczema.

In a preferred embodiment, the vitamin B5 used in the dietary supplement composition is provided in the form of pantothenic acid.

Good results have been obtained using pantothenic acid in the composition in the range of between about 0.1 mg to about 20 mg, more preferably, in the range of between about 0.6 mg to about 10 mg, and optimally in the range of between about 0.8 mg to about 5 mg.

In other embodiments, the vitamin B5 may be provided in other forms including, but not limited to: calcium pantothenate, or as its provitamin, panthenol.

Vitamin B6 assists in the balancing of sodium and potassium as well as promoting red blood cell production within the body of the patient. A vitamin B6 deficiency may cause skin problems, and skin disorders including dermatitis, acne, cracks at corners of the mouth, a smooth and sore tongue, and muscle weakness.

In a preferred embodiment, the vitamin B6 used in the dietary supplement composition is provided in the form of pyridoxine. It has been found that the pyridoxine acts as an antioxidant agent to help prevent the release of histamine within the body, which is known to cause allergic inflammation in patients suffering from such atopic disorders as dermatitis or eczema. It has also been found that pyridoxine, when combined with glycine, taurine, and magnesium, encourages phase 2 liver detoxification of salicylates in the patient, thereby enabling patients suffering from eczema to eat a wider variety of foods without adverse effect.

Good results have been obtained using pyridoxine in the composition in the range of between about 0.1 mg to about 90 mg, more preferably, in the range of between about 0.5 mg to about 50 mg, and optimally in the range of between about 1 mg to about 10 mg.

In other embodiments, the vitamin B6 may be provided in other forms including, but not limited to: pyridoxine hydrochloride, pyridoxal 5'-phosphate (activated form), or any nutritionally acceptable salt of pyridoxine.

Vitamin B7 is necessary for cell growth, the production of fatty acids, and the metabolism of fats and amino acids. A vitamin B7 deficiency may lead to skin disorders including dermatitis, eczematous dermatitis, cracks at corners of the mouth, sores in the mouth, scaly lips, dry skin, and a greyish pallor.

In a preferred embodiment, the vitamin B7 used in the dietary supplement composition is provided in the form of biotin, a B complex growth factor. It has been found that the inclusion of biotin in the dietary supplement composition helps to replenish the balance of this vitamin within the body of patients suffering from such disorders as dermatitis or eczema.

Good results have been obtained using biotin in the composition in the range of between about 1 µg to about 1200 µg, more preferably, in the range of between about 10 µg to about 500 µg, and optimally in the range of between about 30 µg to about 200 µg.

Vitamin B9 is vital to many bodily functions from synthesizing and repairing DNA to influencing and playing a role in the reaction of rapid cell division and growth. Vitamin B9 is during periods of rapid cell division and growth such as infancy and pregnancy. A vitamin B9 deficiency can cause anaemia, pallor and cracks at corners of the mouth, and during pregnancy may cause birth defects therefore supplementation or ingestion of foods high in folic acid should be consumed during pregnancy to prevent this.

In a preferred embodiment, the vitamin B9 used in the dietary supplement composition is provided in the form of folic acid. It has been found that the inclusion of folic acid in the dietary supplement composition helps to replenish the balance of this vitamin within the body of patients suffering from such disorders as dermatitis or eczema.

Good results have been obtained using folic acid in the composition in the range of between about 1 µg to about 600 µg, more preferably, in the range of between about 5 µg to about 200 µg, and optimally in the range of between about 10 µg to about 100 µg.

Vitamin B12 has a key role in the normal functioning of the brain and nervous system, and for the formation of blood. It is normally involved in the metabolism of every cell of the body, especially affecting DNA synthesis and regulation, but also fatty acid synthesis and energy production.

In a preferred embodiment, the vitamin B12 used in the dietary supplement composition is provided in the form of cyanocobalamin. It has been found that the inclusion of cyanocobalamin in the dietary supplement composition helps to replenish the balance of this vitamin within the body of patients suffering from such disorders as psoriasis, eczema or dermatitis.

Good results have been obtained using cyanocobalamin in the composition in the range of between about 1 µg to about 600 µg, more preferably, in the range of between about 5 µg to about 200 µg, and optimally in the range of between about 10 µg to about 100 rig.

Vitamin D is a fat-soluble vitamin that directly and indirectly controls more than 200 genes. Vitamin D is widely used to limit inflammation in the body, assist with breathing ability in asthma sufferers, and help form and maintain bones. It is understood that children with moderate to severe atopic eczema have significantly lower levels of vitamin D compared with children who have mild symptoms. Adults with eczema consume diets lower in vitamin D large role in skin cell metabolism and maintenance, such as the treatment of itchy, flaky skin. Vitamin D also acts as a powerful antioxidant agent which protects against free radical damage and it enhances calcium absorption.

In a preferred embodiment, the vitamin D used in the dietary supplement composition is provided in the form of vitamin D3 (cholecalciferol). It has been found that the inclusion of cholecalciferol in the dietary supplement composition helps to replenish the balance of this vitamin within the body of patients suffering from such disorders as eczema, psoriasis or dermatitis.

Good results have been obtained using cholecalciferol in the range of between about 0.1 µg to about 100 µg, more preferably, in the range of between about 2 µg to about 20 µg, and optimally in the range of between about 5 µg to about 10 µg in the composition.

Dietary minerals are the chemical elements required by living organisms, other than the four elements carbon, hydrogen, nitrogen, and oxygen present in common organic molecules.

The dietary supplement composition further comprises as active ingredients, an effective amount of one or more minerals.

Calcium promotes a healthy acid mantle, which protects the skin barrier from microbe invasion and infections, which is advantageous to eczema and dermatitis sufferers, and those with dry skin.

It has also been found that the inclusion of calcium in the dietary supplement composition helps to maintain the right amount of calcium in the body. Eczema patients are often prescribed a dairy-restricted diet and more than 40 percent of patients are allergic to dairy products so their dietary calcium intake may be low. Most calcium supplements are in sold in large tablet form and are difficult to swallow so compliance is low, making a powder or liquid form advantageous to eczema sufferers.

The calcium used in the dietary supplement composition may be provided in the form of calcium citrate, calcium carbonate, calcium phosphate, hydroxyapatite, or any other nutritionally acceptable calcium salt.

In a preferred embodiment, the calcium is provided in the form of calcium citrate. It has been found that the inclusion of calcium citrate in the dietary supplement composition provides a patient with a form of calcium that does not hamper the digestion of a patient.

Unexpected results have been obtained using calcium citrate in the composition in the range of between about 1 mg to about 3000 mg elemental calcium, more preferably, in the range of between about 100 mg to about 2000 mg, and optimally in the range of between about 400 mg to about 1000 mg.

Copper stimulates the immune system to fight infections, to repair injured tissues, and to promote healing. Copper also helps to neutralize "free-radicals", which can cause severe damage to cells. A copper deficiency may alter the role of other cellular constituents involved in antioxidant activities, such as iron, selenium, and glutathione, and therefore plays an important role in diseases in which oxidant stress is elevated.

The copper used in the dietary supplement composition may be provided in the form of copper gluconate, cupric oxide or any other nutritionally acceptable copper salt.

In a preferred embodiment, the copper is provided in the form of copper gluconate. It has been found that the inclusion of copper gluconate in the dietary supplement composition helps to neutralize free-radicals formed within the body due to oxidative stress, which can cause severe damage to cells.

Good results have been obtained using copper gluconate in the composition in the range of between about 0.01 mg to about 15 mg elemental copper, more preferably, in the range of between about 0.05 mg to about 10 mg, and optimally in the range of between about 0.1 mg to about 2 mg.

Chromium stimulates the activity of enzymes involved in glucose metabolism for energy and the synthesis of fatty acids. It also increases the effectiveness of insulin, helping the transport of glucose into cells. A chromium deficiency may be a factor that will upset the function of insulin resulting in elevated insulin levels in the blood, which prevents dihomo gamma-linolenic acid (DGLA) from being converted to series 1 prostaglandins (PGE1), which promotes skin hydration.

The chromium used in the dietary supplement composition may be provided in the form of chromium amino acid chelate, chromium chloride, chromium nicotinate, high-chromium yeast, chromium citrate, or any other nutritionally acceptable chromium salt.

In one embodiment, the chromium used in the dietary supplement composition is provided in the form of chromium picolinate. It has been found that the inclusion of chromium picolinate in the dietary supplement composition helps to reduce high blood sugar and the need for high insulin levels needed within the body of patients suffering from such disorders as dermatitis or eczema, thereby promoting the conversion of DGLA into PGE1, which has the effect of reducing the inflammation associated with such disorders.

Good results have been obtained using chromium picolinate in the composition in the range of between about 1 μg to about 1200 μg elemental chromium, more preferably, in the range of between about 5 μg to about 500 μg, and optimally in the range of between about 10 μg to about 60 μg.

Magnesium is involved in many essential metabolic processes. Most magnesium is found inside of cells, where it activates enzymes necessary for the metabolism of carbohydrates and amino acids. Magnesium helps promote absorption and metabolism of other minerals, like calcium, phosphorus, sodium and potassium. It also helps utilize the B-complex, vitamins C and E in the body.

In preferred embodiments, the magnesium used in the dietary supplement composition may be provided in the form of magnesium oxide, magnesium gluconate, magnesium phosphate, or any other nutritionally acceptable magnesium salt thereof.

In some embodiments, the magnesium used in the dietary supplement composition is provided in the form of magnesium glycinate. It has been found that the inclusion of magnesium glycinate in the dietary supplement composition, when combined with glycine, vitamin B6, and taurine, encourages phase 2 liver detoxification of salicylates in the patient, thereby enabling patients suffering from such disorders as dermatitis or eczema, to eat a wider variety of foods without adverse effect.

Good results have been obtained using magnesium glycinate in the composition in the range of between about 5 mg to about 600 mg elemental magnesium, more preferably, in the range of between about 10 mg to about 400 mg, and optimally in the range of between about 15 mg to about 280 mg.

Manganese is an essential element that helps the body form bones, connective tissue and collagen within the skin. Manganese is involved in the metabolism of carbohydrates and amino acids and it plays a role in calcium absorption and blood sugar regulation.

In preferred embodiments, the manganese used in the dietary supplement composition may be provided in the form of manganese amino acid chelate, manganese gluconate, manganese sulfate, or any other nutritionally acceptable magnesium salt thereof.

In a preferred embodiment, it has been found that the inclusion of manganese amino acid chelate in the dietary supplement composition helps to replenish the balance of this mineral within the body of patients suffering from such disorders as dermatitis or eczema.

Good results have been obtained using manganese amino acid chelate in the composition in the range of between about 0.1 mg to about 10 mg elemental manganese, more preferably, in the range of between about 0.2 mg to about 5 mg, and optimally in the range of between about 0.5 mg to about 2 mg.

Molybdenum is a facilitator of liver detoxification in the sulphation pathway. Molybdenum also plays a vital role in regulating the metabolism of certain minerals within the body, including: calcium, magnesium, and copper, and facilitating the body's use of iron, which is necessary for normal growth and development.

Molybdenum also functions as a cofactor for a number of enzymes that catalyse important chemical transformations in the global carbon, nitrogen, and sulfur cycles. In particular, molybdenum is the cofactor for human enzymes, including xanthine oxidase, sulfite oxidase, and aldehyde oxidase. In humans, xanthine oxidase is normally found in the liver and is released into the blood if liver damage has happened. Aldehyde oxidase is a molybdenum cofactor-containing soluble enzyme present in the liver and other tissues of several mammalian species.

The molybdenum used in the dietary supplement composition refers to trace elemental molybdenum, or any of its nutritionally acceptable salts.

In a preferred embodiment, it has been found that the inclusion of trace elemental mineral within the body of patients suffering from skin diseases such as eczema and psoriasis.

Unexpected results have been obtained using elemental molybdenum in the composition in the range of between about 2 μg to about 2000 μg elemental molybdenum, more preferably, in the range of between about 10 μg to about 500 μg, and optimally in the range of between about 20 μg to about 200 μg.

In other embodiments, the molybdenum may be provided in other forms including, but not limited to: sodium molybdate, ammonium molybdate, or any combination of the above.

Zinc has a variety of functions. It is important for growth and development, immune response, and neurological and reproductive functions. It is also related to the normal absorption of vitamins especially the B complex. A zinc deficiency may retard growth, prolong wound healing and sexual maturity.

In a preferred embodiment, the zinc used in the dietary supplement composition may be provided in the form of zinc oxide, zinc gluconate, or any other nutritionally acceptable zinc salt.

In a preferred embodiment, the zinc used in the dietary supplement composition is provided in the form of zinc picolinate. It has been found that the inclusion of zinc picolinate in the dietary supplement composition plays a wound healing role by encouraging cell and tissue growth, particularly in patients suffering from such skin disorders as dermatitis or eczema.

Good results have been obtained using zinc picolinate in the composition in the range of between about 0.1 mg to about 90 mg elemental zinc, more preferably, in the range of between about 1 mg to about 50 mg, and optimally in the range of between about 2 mg to about 10 mg.

It is believed that zinc and copper compete for absorption in the digestive tract so that a diet that is excessive in one of these minerals may result in a deficiency in the other therefor copper has been included in the invention.

In addition to these active ingredients, the dietary supplement composition still further comprises other ingredients, added alone or in combination, including taurine, and beta-carotene.

Taurine is derivative of the amino acid cysteine. Taurine, often referred to as an amino acid, is not part of the human body's structural proteins. Instead, taurine remains free in the tissues and bloodstream.

In a preferred embodiment, it has been found that the inclusion of taurine in the dietary supplement composition when combined with glycine, vitamin B6, and magnesium, encourages phase 2 liver detoxification of salicylates in the patient, thereby enabling patients suffering from such disorders as dermatitis or eczema, to eat a wider variety of foods without adverse effect.

Good results have been obtained using taurine in the composition in the range of between about 1 mg to about 2000 mg, more preferably, in the range of between about 2 mg to about 100 mg, and optimally in the range of between about 3 mg to about 30 mg.

Beta-carotene is a pigment found in plants and it functions as an antioxidant. Beta-carotene is important for reducing sun sensitivity and it increases UV sun protection within the skin, which is advantageous for those with eczema or dermatitis.

In a preferred embodiment, it has been found that the inclusion of beta-carotene in the dietary supplement composition helps to replenish the balance of this nutrient within the body of patients suffering from such disorders as dermatitis or eczema.

Good results have been obtained using beta-carotene in the range of between about 1 µg to about 2000 µg, more preferably, in the range of between about 100 µg to about 1000 µg, and optimally in the range of between about 500 µg to about 700 µg in the composition.

While some of the aforementioned ingredients are available in common multivitamin/multi-mineral supplement, they are not provided with glycine and taurine, or available in the combinations or quantities believed to be necessary for use in treating atopic skin disorders such as dermatitis or eczema as disclosed herein.

In accordance with another preferred embodiment of the present invention, the dietary supplement composition comprises as active ingredients in a total daily dosage: at least one nutrient selected from the group comprising of about 5 mg to about 7000 mg glycine, about 1 mg to about 3000 mg calcium; and at least one nutrient selected from the group comprising of about 5 mg to about 2000 mg vitamin C (ascorbic acid), about 1 mg to about 1200 mg vitamin E. These active ingredients have been shown to have good effect on patients suffering from eczema.

In addition to these active ingredients, the dietary supplement composition can further comprise other vitamins and minerals, added alone or in combination: vitamin B1 (thiamine), vitamin B2 (riboflavin), vitamin B3 (niacin), vitamin D3 (cholecalciferol), vitamin B5 (pantothenic acid), vitamin B6 (pyridoxine), vitamin B7 (biotin), vitamin B9 (folic acid), vitamin B12 (cyanocobalamin), magnesium (magnesium glycinate), manganese (manganese amino acid chelate), copper (copper gluconate), chromium (chromium picolinate), molybdenum (elemental molybdenum), and zinc (zinc picolinate).

It will be appreciated that any combination of these active ingredients might be included in the dietary supplement composition.

The delivery of effective quantities of the above active ingredients of the dietary supplement composition may be accomplished through oral administration of single or multiple units given at one time or multiple times throughout the day.

In preferred embodiments, the dietary supplement composition is formulated for oral ingestion in a solid, semi-solid, or liquid form by combining the active ingredients of the composition with one or more suitable excipients.

Solid dosage forms for oral administration include capsules, tablets, pills, powders, gummies, and granules. Solid dosage forms of preferred embodiments of the present invention may be produced using any pharmaceutically acceptable excipients including any one or more of the following binders: proteins such as polysaccharides such as starch, cellulose, methyl cellulose, carboxymethylcellulose, cellulose ether, gelatin, natural sugars (e.g., sucrose, glucose or beta-lactose), xylitol, corn sweeteners, natural and synthetic gums (e.g., acacia, xanthan gum, tragacanth or sodium alginate), polymers such as polyvinylpyrrolidone and polyethylene glycol, as well as calcium, magnesium, sodium bicarbonate, protein powder, rice flour, glycine, lysine, taurine, chlorella, beta-carotene, waxes, and the like.

For example, in the case of tablets, these may be formed by combining all of the active ingredients with one or more suitable binders through a simple mixing process. The resulting the active ingredients within the tablet from deterioration by moisture in the air. An enteric coating may be used to provide selective disintegration in, e.g., the gastrointestinal tract. For most coated tablets, a cellulose ether hydroxypropyl methylcellulose (HPMC) film coating is used which is free of sugar and potential allergens. Occasionally, other coating materials are used, for example synthetic polymers, shellac, corn protein, zein, or other polysaccharides.

The tablet may be manufactured as immediate-release, mixed-release or sustained-release formulations to provide for a range of release of the active ingredients within the dietary supplement composition over a period of minutes to hours.

The tablets may also comprise suitable lubricants, disintegrating agents, colouring agents, 10 flavouring agents, flow-inducing agents, gummy agents, chewing agents and/or melting agents as required.

In other embodiments, the dietary supplement composition may be prepared for oral ingestion in liquid dosage form. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents, mixtures thereof, and the like. Liquid dosage forms for oral administration may also include colouring and flavouring agents.

In other embodiments, the dietary supplement composition may be prepared for oral ingestion in a powder or granule form, either by itself, or by encapsulating the powder or granules within a hard or soft gelatin capsule, together with one or more suitable powdered inert carriers such as, for example, lactose, starch, a cellulose derivative, magnesium stearate, stearic acid, dicalcium phosphate, and the like. Such powdered or granule dosage forms may contain, for example, suitable solvents, preservatives, emulsifying agents, suspending agents, diluents, sweeteners, thickeners, protein powders, and melting agents, mixtures thereof, and the like.

Powdered or granule dosage forms for oral administration may also comprise suitable 30 lubricants, disintegrating agents, colouring agents, flavouring agents, flow-inducing agents and/or gummy agents as required.

For adults, the dietary supplement composition is typically administered orally at daily dosage of from about 0.1 g to about 25 g per day, more preferably, from about 3 g to about 20 g per day, and optimally, from about 5 g to about 15 g per day. It will be appreciated however, that the daily dosage may vary from patient to patient.

Patients suffering from eczema are known to present with salicylate sensitivity, which worsens after ingesting salicylate-containing foods (found in many healthy foods, fruits and vegetables, sauces and juices). By incorporating effective amounts of glycine, vitamin B6, molybdenum, and magnesium in the dietary supplement composition, it was found that these active ingredients encourage a phase 2 detoxification reaction to occur in the liver, which causes any salicylates, tartrazine, or preservatives (such as benzoic acids and sulfites) passing via the bloodstream within the liver to be deactivated, thereby enabling them to be removed from the body. As a benefit, such patients are able to eat a wider variety of foods without a noticeable worsening of their eczema or psoriasis.

Patients suffering from eczema are known to have elevated histamine levels in their blood combined with a reduced capacity to detoxify these histamines. The release of histamine within the body is known to cause allergic inflammation in such patients. By incorporating effective amounts of vitamin C and vitamin B6, in the dietary supplement composition, it was found that each of these active ingredients has the effect of increasing diamine oxidase (DAO) activity within the body which causes the histamine to break down, thereby reducing the level of histamine in the patient.

In series 2 prostaglandin synthesis, the formation of leukotriene B4, a 5-lipoxygenase metabolite of arachidonic acid, is known to promote the pathogenesis of atopic and non-atopic eczema in patients, while leukotriene formation is known to prolong the inflammatory process in such patients. By incorporating effective amounts of vitamin E, in the dietary supplement composition; it was found that each of these active ingredients has the effect of inhibiting lipoxygenase and leukotriene B4 formation in patients, thereby reducing their respective adverse effects on the patient.

Patients suffering from eczema are known to have elevated serum IgE levels in their blood. By incorporating effective amounts of vitamin C in the dietary supplement composition, it was found that each of these active ingredients has the effect of recycling vitamin E within the body of the patient. As a benefit, the recycled vitamin E can be circulated around the body to help lower serum IgE concentrations, thereby resulting in a lower frequency of allergen sensitisation.

Certain omega-6 fatty acids such as arachidonic acid are known to cause inflammation within the body. While other fatty acids such as gamma linolenic acid (GLA) may actually reduce inflammation when they are converted to the omega-6 metabolite, DGLA and then converted to PGE1. Patients suffering from eczema tend to have elevated omega-6 levels in their blood and adipose tissue, in conjunction with a decrease in DGLA. The conversion of DGLA to PGE1 can be blocked by high insulin levels. By incorporating effective amounts of elemental chromium in the dietary supplement composition, it was found that this active ingredient has the effect of reducing high insulin levels, thereby promoting the conversion of DGLA to PGE1 within the body.

The inclusion of chromium in the dietary supplement composition assists in the breakdown of proteins, carbohydrates, and fats within the body.

The following examples are put forth so as to provide persons skilled in the art with a complete disclosure and description of how to make and use the compositions according to the preferred embodiments of the present invention, and is not intended to limit the scope of the present invention.

Efforts have been made to ensure accuracy with respect to numbers (e.g. amounts, temperature, etc.) but some errors and deviations should be accounted for. Unless indicated otherwise, parts are parts by weight, temperature is in [deg.] C. and pressure is at or near atmospheric pressure.

Several studies were conducted using the following dietary supplement compositions (Samples #1 to #6), which were orally administered to adult and child patients. The dietary supplement compositions used to prepare these samples are listed in Tables 1, 2 and 3, which include the dosage value of each ingredient within the compositions.

EXAMPLE 1

Each dietary supplement composition was orally administered to patients suffering from dermatitis or eczema over a period of about 4 to 8 weeks. Supplementary dietary compositions according to Sample #1 and Sample #2 (see Table 1 below) were tested on eczema patients for four weeks. The child dose was approximately a quarter of the adult dose. Micrograms are denoted using μg.

TABLE 1

| Nutrient | Child Dosage Sample #1 (mg) | Adult Dosage Sample #2 (mg) |
| --- | --- | --- |
| Glycine | 125-375 | 400-1200 |
| Vitamin C (ascorbic acid) | 40 | 160 |
| Quercetin | 30 | 120 |
| Magnesium (magnesium glycinate) | 25 | 100 |
| Coenzyme Q10 | 10 | 40 |
| Alpha lipoic acid | 10 | 40 |
| Zinc (zinc picolinate) | 6 | 14 |
| Vitamin E (d-alpha tocopheryl succinate) | 5 | 20 |
| Taurine | 5 | 20 |
| Vitamin B6 (pyridoxine) | 2 | 8 |
| Choline | 2 | 8 |
| Inositol | 2 | 8 |
| Vitamin B5 (pantothenic acid) | 1 | 4 |
| Copper (copper gluconate) | 0.5 | 2 |
| Vitamin B1 (thiamine) | — | — |
| Vitamin B3 (niacin) | — | — |
| Potassium (potassium citrate) | — | — |
| Rice flour | | |
| Molybdenum | 45 μg | 180 μg |
| Vitamin B7 (biotin) | 40 μg | 160 μg |
| Vitamin D3 (cholecalciferol) | 5 μg | 10 μg |
| Vitamin D3 (cholecalciferol) | 5 μg | 10 μg |
| Vitamin K1 (phylloquinone) | 25 μg | 100 μg |
| Chromium (chromium picolinate) | 15 μg | 60 μg |
| Vitamin B9 (folic acid) | 15 μg | 60 μg |
| Vitamin B12 (cyanocobalamin) | 15 μg | 60 μg |

Two out of six patients experienced an improvement in their skin condition. However, some moderate adverse effects were noted, which were attributed to the alpha lipoic acid, potassium and/or quercetin. The formula was modified and the adverse effects subsided.

EXAMPLE 2

Dietary supplement compositions shown in Table 2 (see below) were orally administered to patients suffering from dermatitis or eczema over a period of about 4 to 8 weeks. The composition in Sample #3 was modified and tested on eczema patients for six weeks. International units are denoted using IU. 400 IU=10 μg.

TABLE 2

| Nutrient | Adult Dosage Sample #3 (mg) | Adult Dosage Sample #4 (mg) |
| --- | --- | --- |
| Glycine | — | 800 |
| Calcium (calcium citrate) | — | 500 |
| Vitamin C (ascorbic acid) | 50 | 50 |
| Magnesium (magnesium glycinate) | 60 | 60 |
| Zinc (zinc picolinate) | 4 | 4 |
| Vitamin E (d-alpha tocopheryl succinate) | 20 | 20 |
| Taurine | 20 | 20 |
| Vitamin B6 (pyridoxine) | 3 | 3 |
| Manganese (amino acid chelate) | 1 | 1 |
| Vitamin B1 (thiamine) | 1 | 1 |
| Vitamin B2 | 1 | 1 |
| Vitamin B3 (niacin) | 1 | 1 |
| Vitamin B5 | 1 | 1 |
| Copper (copper gluconate) | 200 μg | 200 μg |
| Beta-carotene | 600 μg | 600 μg |
| Vitamin B7 (biotin) | 200 μg | 200 μg |
| Molybdenum | 45 μg | 45 μg |
| Vitamin D3 (cholecalciferol) | 400 IU | 400 IU |
| Chromium (chromium picolinate) | 45 μg | 45 μg |
| Folic acid | 50 μg | 50 μg |
| Vitamin B12 (cyanocobalamin) | 5 μg | 5 μg |

For sample #3, no adverse, or significant positive results were noted. The composition was substantially free of the active ingredients glycine and calcium and has a less than moderate effectiveness.

Glycine and calcium were added to Sample #4. The results showed no adverse symptoms and three out of five patients experienced an improvement in sleep. However, only minor physical improvement in the skin condition was noted, and the reduced positive effects was attributed to the addition of calcium which blocks the absorption of other nutrients.

EXAMPLE 3

Sample #5 and Sample #6 were tested on eczema patients. These samples were divided into two separate containers and presented as a unique day-night formula, which provided unexpected results during testing, including improved sleep and decreased rash in sufferers of eczema. Dietary supplement compositions shown in Table 3 (see below) were orally administered in a two-part dosage form to patients suffering from dermatitis or eczema over a period of about 4 to 8 weeks. Sample #6 was tested on non-atopic patients for four weeks.

TABLE 3

| Nutrient | Adult Dosage Sample #5 (mg) | Adult Dosage Sample #6 (mg) |
| --- | --- | --- |
| Glycine | 1000 | 50 |
| Protein powder (Glycine content) | — | 10 g (400 mg) |
| Vitamin C (magnesium ascorbate) | 50 | 50 |
| Magnesium (magnesium glycinate) | 60 | 60 |
| Coenzyme Q10 | — | 30 |
| Zinc (zinc picolinate) | 4 | 4 |
| Vitamin E (d-alpha tocopheryl succinate) | 20 | 20 |
| Taurine | 20 | 20 |
| Vitamin B6 (pyridoxine) | 3 | 3 |
| Manganese (amino acid chelate) | 1 | 1 |
| Vitamin B1 (thiamine) | 1 | 1 |
| Vitamin B2 | 1 | 1 |
| Vitamin B3 (niacin) | 1 | 1 |
| Vitamin B5 | 1 | 1 |
| Copper (copper gluconate) | 200 μg | 200 μg |
| Beta-carotene | 600 μg | 600 μg |
| Vitamin B7 (biotin) | 200 μg | 200 μg |
| Molybdenum | 45 μg | 45 μg |
| Chromium (chromium picolinate) | 45 μg | 45 μg |
| Folic acid | 50 μg | 50 μg |
| Vitamin B12 (cyanocobalamin) | 5 μg | 5 μg |
| Calcium (calcium citrate)* | 800 | 800 |
| Vitamin D3 (cholecalciferol)* | 400 IU | 400 IU |
| Magnesium (magnesium glycinate)* | 160 | 160 |

*Active ingredients, taken in a separate 'night' supplement.

The results of Sample #5 showed that patients suffering from eczema reported a significant improvement in their skin condition after the test period, with three out of six patients showing a complete recovery. Four out of six patients reported improved sleep, and four out of six patients had decreased itch and rash symptoms. The unexpected results were attributed to the inclusion of glycine and calcium, and by dividing the formula so the calcium did not affect the absorption of the other active ingredients.

It was also found that when patients stopped taking the dietary supplement composition, many of the symptoms returned.

The results of Sample #6 found the general health and wellbeing of non-atopic patients improved, with five out of six patients reporting increased energy. Five out of six patients reported improved overall skin condition and three out of six patients experienced decreased skin roughness. Some adverse effects were however noted and believed to be attributable to coenzyme Q10 and copper.

EXAMPLE 4

Patients with eczema symptoms are treated with a day/night dosage regimen for up to 12-weeks with a morning dose of a first dietary supplement composition and a nightly dose of a second complementary dietary composition according to Table 4.

In these examples, composition part 1 and 2 were ingested in powdered form, and dosage of powder measured with a 1 g mini-scoop. Patients were trialed using a 2 g dose of composition part 1, and a 5 g dose of composition part 2.

TABLE 4 part 1 of dietary supplement treatment composition

| Component | Adult Dosage Sample #7 | Child Dosage Sample #8 |
| --- | --- | --- |
| Glycine | 800 mg | 400 mg |
| Magnesium (Magnesium glycinate) | 120 mg | 60 mg |
| Molybdenum | 45 μg | 22.5 μg |
| Chromium (chromium picolinate) | 40 μg | 20 μg |
| Vitamin E (d-alpha tocopheryl succinate) | 40 mg | 20 mg |
| Vitamin B1 | 1.2 mg | 0.6 mg |
| Vitamin B2 | 1.2 mg | 0.6 mg |

TABLE 4-continued part 1 of dietary supplement treatment composition

| Component | Adult Dosage Sample #7 | Child Dosage Sample #8 |
|---|---|---|
| Vitamin B3 | 2 mg | 1 mg |
| Pyridoxine (Vitamin B6) | 2 mg | 1 mg |
| Biotin (Vitamin B7) | 30 μg | 15 μg |
| Vitamin B12 (cyanocobalamin) | 10 μg | 5 μg |
| Magnesium ascorbate* (micronized to enhance absorption of Vitamin C) | 60 mg | 30 mg |
| Zinc (zinc picolinate) | 8 mg | 4 mg |
| Fillers | 200 mg | 100 mg |

TABLE 5

Part 2 of the dietary supplement composition treatment

| Component | Adult dosage | Child dosage |
|---|---|---|
| Calcium (calcium citrate and calcium carbonate), micronized* | 1000-1100 mg | 500-550 mg |
| Magnesium (magnesium glycinate), micronized | 120 mg | 60 mg |
| Vitamin D3 | 20 ug | 10 ug |

People with eczema commonly have poor digestion and absorption, which contributes to eczema symptoms, so we employ a unique processing technique for the preparation of the calcium and magnesium in our composition. Micronization is a manufacturing technique for refining and enhancing overall bioavailability of a solid nutrient.

Results

As will be shown in the figures, using the dietary supplement composition has a significant and visible effect on eczema and psoriasis. For example, FIG. 1A illustrates one embodiment of chronological results of an arm associated with the dietary supplement composition. Specifically, FIG. 1A shows an arm before treatment. FIG. 1B illustrates one embodiment of chronological results of the arm after one week of treatment with the dietary supplement composition. FIG. 1C illustrates one embodiment of chronological results of the arm after 12 weeks of treatment with the dietary supplement composition.

Figures 2A, 2B, 2C:
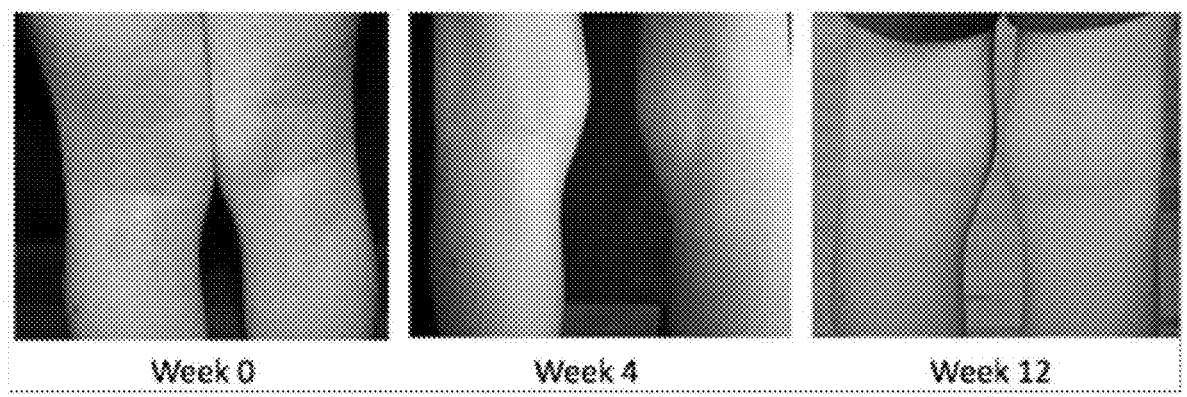
FIG. 2A illustrates one embodiment of chronological results of a leg associated with a dietary supplement composition as a prophylactic and treatment for skin diseases such as eczema and psoriasis and the like and method of treatment.
FIG. 2B illustrates one embodiment of chronological results of a leg associated with a dietary supplement composition as a prophylactic and treatment for skin diseases such as eczema and psoriasis and the like and method of treatment.
FIG. 2C illustrates one embodiment of chronological results of a leg associated with a dietary supplement composition as a prophylactic and treatment for skin diseases such as eczema and psoriasis and the like and method of treatment.

In another example, FIG. 2A illustrates one embodiment of chronological results of legs associated with the dietary supplement composition. Specifically, FIG. 1A shows the legs before treatment. FIG. 2B illustrates one embodiment of chronological results of the legs after four weeks of treatment with the dietary supplement composition. FIG. 2C illustrates one embodiment of chronological results of the legs after 12 weeks of treatment with the dietary supplement composition.

Figures 3A, 3B, 3C:
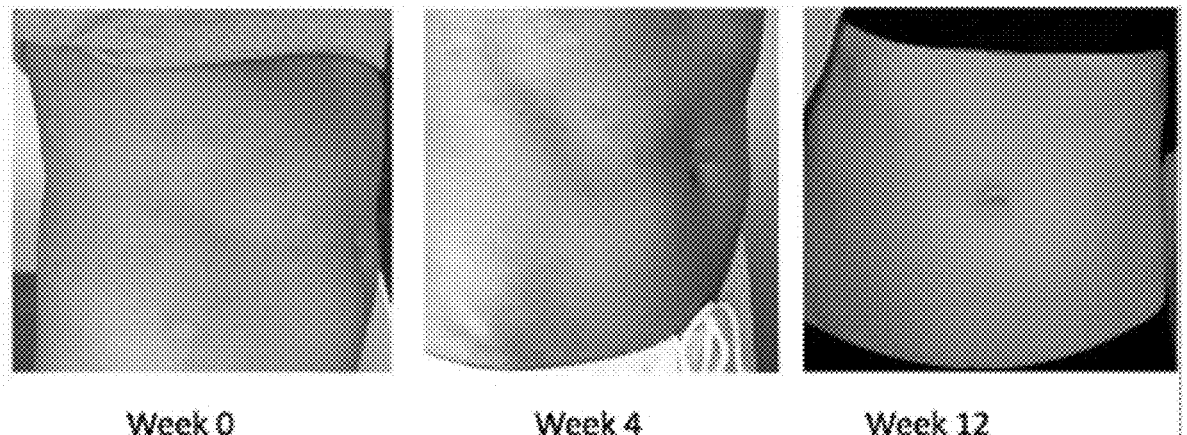
FIG. 3A illustrates one embodiment of chronological results of a torso associated with a dietary supplement composition as a prophylactic and treatment for skin diseases such as eczema and psoriasis and the like and method of treatment.
FIG. 3B illustrates one embodiment of chronological results of a torso associated with a dietary supplement composition as a prophylactic and treatment for skin diseases such as eczema and psoriasis and the like and method of treatment.
FIG. 3C illustrates one embodiment of chronological results of a torso associated with a dietary supplement composition as a prophylactic and treatment for skin diseases such as eczema and psoriasis and the like and method of treatment.

In another example, FIG. 3A illustrates one embodiment of chronological results of a torso associated with the dietary supplement composition. Specifically, FIG. 3A shows the torso before treatment. FIG. 3B illustrates one embodiment of chronological results of the torso after four weeks of treatment with the dietary supplement composition. FIG. 3C illustrates one embodiment of chronological results of the torso after 12 weeks of treatment with the dietary supplement composition.

As can be seen, the treatments have shown dramatic improvements in a patient's symptoms over a short period of time. The present treatment regimen represents an advance over prior art treatments of skin diseases including eczema, psoriasis, dermatitis and allergic skin diseases.

Applicant's treatments have shown dramatic improvements in a patient's symptoms over a short period of time. The present treatment regimen represents an advance over prior art treatments of skin diseases including eczema, psoriasis, dermatitis and allergic skin diseases.

Figure 4:
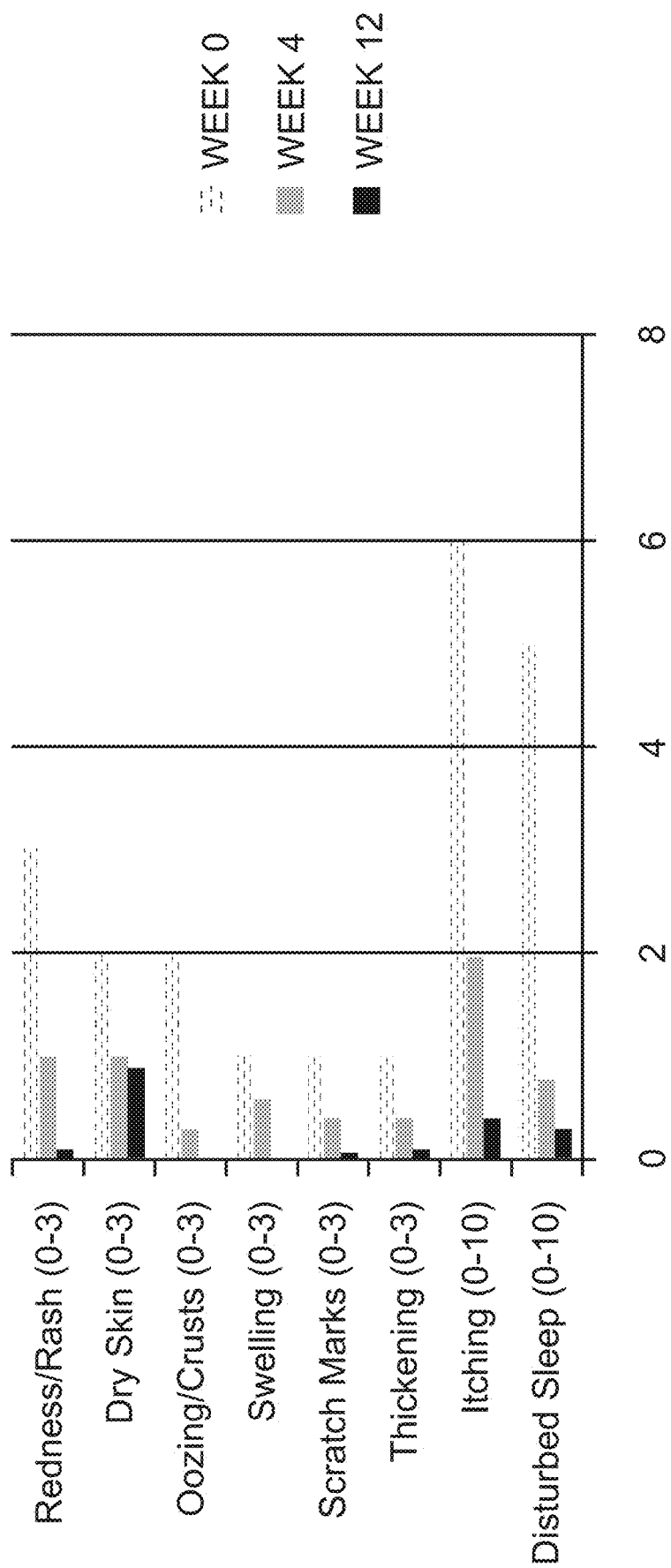
FIG. 4 is a graph depicting results of the study of the compositions used in Table 4 and 5.

The present treatment also reduces side-effects and risks associated with conventional treatments of children such as with topical hydrocortisone on irritated or broken skin, and avoids thinning of the skin. FIG. 4: results of compositions used in Table 4 and 5.

Diagram notes for FIG. 4: Using the official SCORAD (scoring atopic dermatitis) method for measuring eczema symptoms, 30 eczema patients were photographed and the severity of their eczema symptoms were documented at week 0 (group average shown in green), week 4 (shown in red) and week 12 (final group results shown in blue) were rated from 0 to 3, with 3 being the most severe manifestation. Itching and disturbed sleep were rated from 0 to 10, with 10 being the most severe disturbance.

Participants were given the two-part composition and instructed to take the AM formula with breakfast and the PM (calcium, magnesium and vitamin D) composition in the afternoon in order to increase absorption and reduce nutrient interactions (as high dose calcium blocks zinc absorption). Participants were instructed to keep the rest of their daily routine and diet the same as before.

The dietary supplement composition significantly reduced eczema symptoms within 28 days (shown in red in diagram 1). By week 12, 90% of patients showed statistically significant improvements in eczema symptoms and 75% recorded complete remission of eczema symptoms. The two people who presented with moderate psoriasis had complete remission of psoriasis by week 12. No side-effects were noted and long-term use and safety has been established.

It is believed that calcium supplementation blocks the absorption of medical drugs and minerals including zinc. For this reason, calcium is contraindicated when taking medications or in cases of mineral deficiencies, particularly zinc as in the case of psoriasis and eczema. Hence the dietary supplement composition in example 4 of the invention was divided into two separate containers and presented as a unique day-night formula (also refer example 3 Tables 5 and 6), which provided unexpected results during testing, including improved sleep and decreased rash in sufferers of eczema.

This represents a significant increase in the effectiveness of the treatment regimen, when compared with previous trials.

EXAMPLE 5

Patients with eczema symptoms are treated with a day/night dosage regimen for up to 12-weeks with a morning dose of a first dietary supplement composition and a nightly dose of a second complementary dietary composition according to Table 4. In these examples (see Tables 6 and 7), composition part 1 and 2 were ingested in powdered form, and dosage of powder measured with a 1 g mini-scoop. Patients were trialed using 2 g doses for part 1 and 5 g doses of part 2. The composition of part 1 and 2 are ingested in powder form. Part 1: the daily dose of powder is measured with a 1 g mini-scoop. Children were given 1 mini-scoop daily and parents were advised to mix the powder into water or food and serve it with breakfast.

TABLE 6 childhood eczema patient formula
(morning composition, part 1)

| Component | Child Dosage Sample #9 |
|---|---|
| Glycine | 200 mg |
| Molybdenum | 5 μg |
| Magnesium (50 mg total) | 10 mg |
| Chromium (chromium picolinate) | 5 μg |
| Vitamin E (d-alpha tocopheryl succinate) | 5 mg |
| Vitamin C (Magnesium ascorbate* (micronized to enhance absorption) | 10 mg |
| Vitamin B1 | 0.3 mg |
| Vitamin B2 | 0.3 mg |
| Vitamin B3 | 1 mg |
| Pyridoxine | 0.6 mg |
| Biotin (vitamin B7) | 5 μg |
| Vitamin B12 (cyanocobalamin) | 1 μg |
| Zinc (zinc picolinate) | 1 mg |
| Filler | 200 mg |

TABLE 7 childhood eczema patient
formula (afternoon formula, part 2)

| Component | Child dosage Sample #9 |
|---|---|
| Calcium (calcium citrate and calcium carbonate) | 200 mg |
| Magnesium (magnesium glycinate) | 40 mg |
| Vitamin D3 | 1 μg |
| Natural flavouring, | 100 mg |

The 2-part composition, detailed in Table 6 and Table 7, contains low doses of all components/nutrients to suit infant patients. It was prescribed to five young patients aged between to 15 months old, rated with 'moderate' childhood eczema (moderate SCORAD range is 25-50, and the patient group average was 40).

After 12 weeks of use, all five children had visible and statistically significant reductions in eczema symptoms (new SCORAD average was 15), and two out of five had a complete remission of eczema symptoms.

EXAMPLE 6

The composition part 1 and part 2 are ingested in powder form. Part 1: Patients suffering from psoriasis were advised to mix 5 g (1 teaspoon) of the powder into water or juice and serve it with breakfast.

TABLE 8

Adult psoriasis (morning dietary supplement composition, part 1)

| Component | Adult Dosage (psoriasis) Sample #10 |
|---|---|
| Glycine | 3000 mg |
| Molybdenum | 200 μg |
| Magnesium (mg glycinate) | 250 mg (elemental) |
| Chromium (chromium picolinate) | 150 μg |
| Vitamin E (d-alpha tocopheryl succinate) | 80 mg |
| Vitamin C (Magnesium ascorbate) | 200 mg (elemental) |
| Vitamin B1 | 10 mg |
| Vitamin B2 | 6 mg |
| Vitamin B3 | 10 mg |
| Pyridoxine | 50 mg |
| Biotin (vitamin B7) | 300 μg |
| Vitamin B12 (cyanocobalamin) | 100 μg |
| Zinc (zinc picolinate) | 15 mg (elemental) |
| Filler | ?? mg |

TABLE 9

Adult psoriasis afternoon
dietary supplement composition, part 2

| Nutrient (part 2 of composition) | Adult dosage (Sample #10) |
|---|---|
| Calcium (calcium citrate and calcium carbonate) | 1500 mg |
| Magnesium (450 g total) (magnesium glycinate) | 200 mg |
| Vitamin D3 | 19 μg |
| Filler (including flavouring, coloring) | ?? mg |

Afternoon formula, Part 2: Patients were advised to mix 5 g (1 teaspoon) of the powder into water or non-dairy milk and take it in the afternoon, in between meals (and not within 2 hours of taking medications). The 2-part composition, detailed in Table 8 and Table 9, was given to adult patients with moderate psoriasis over a 12-week period.

After 12 weeks of use, 4 out of 5 patients had visible and statistically significant reductions in psoriasis symptoms and 3 out of 5 patients had a complete remission of psoriasis symptoms.

EXAMPLE 7

General skin health single dietary supplementary composition. Daily adult dosage is 1 teaspoon per day mixed into water or juice. This is consumed as a prophylactic treatment.

TABLE 10

General skin health composition—
Single composition, powder formula

| Component | Adult Dosage |
|---|---|
| Glycine | 60-80 mg |
| Molybdenum | 45 μg |
| Magnesium | 30 mg |
| Chromium (chromium picolinate) | 25 μg |
| Vitamin E (d-alpha tocopheryl succinate) | 10 mg |
| Vitamin C (calcium ascorbate) | 25 mg |
| Vitamin B1 | 1.1 mg |
| Vitamin B2 | 1.1 mg |
| Vitamin B3 | 5 mg |
| Pyridoxine | 2 mg |
| Biotin (vitamin B7) | 15 μg |
| Vitamin B12 (cyanocobalamin) | 5 μg |
| Vitamin D3 | 5 μg |
| Zinc (zinc picolinate) | 2 mg |
| Fillers, flavours, colouring agents | 1000 μg |

Glycine and calcium dosages are lower (calcium from calcium ascorbate). Prophylactic treatment was shown to significantly reduce return of skin symptoms.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specification.

Embodiments, with each claim standing on its own as a separate embodiment of this invention. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the description provided herein, numerous specific details are set forth. However, it is understood that embodiments of the invention may be practiced without these specific details. In other instances, well-known methods, structures and techniques have not been shown in detail in order not to obscure an understanding of this description.

In describing the preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar manner to accomplish a similar technical purpose. Terms such as "forward," "rearward," "radially," "peripherally," "upwardly," "downwardly," and the like are used as words of convenience to provide reference points and are not to be construed as limiting terms.

It must be noted that, as used in this specification and the appended claims, the singular forms "a," "an" and "the" include plural referents unless the context clearly dictates otherwise.

In describing and claiming the present invention, the following terminology will be used in accordance with the definitions set out below.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. The present method of "treating" a patient, as the term is used herein, thus encompasses both prevention of a disorder in a predisposed individual and treatment of the disorder in a clinically symptomatic individual.

The term "dietary supplement composition" as used herein refers to a preparation comprising one or more nutrients, including, but not limited to, amino acids, proteins, vitamins, minerals, antioxidant agents, anti-inflammatory agents, and precursors, derivatives, metabolites, constituents, concentrates, or extracts of any of these.

The term "active ingredient" as used herein refers to a chemical material or compound that induces a desired effect, and includes ingredients that are therapeutically effective or prophylactically effective.

The term "effective amount" as used herein refers to the amount that will provide a beneficial nutritional effect or response in a patient. For example, as nutritional response to vitamin- and mineral-containing dietary supplement compositions varies from patient to patient, it should be understood that nutritionally effective amounts of the vitamins and minerals will vary, respectively. Thus, while one patient may require a particular profile of vitamins and minerals present in defined amounts, another patient may require the same particular profile of vitamins and minerals present in different defined amounts.

The term "antioxidant agent" as used herein refers to any molecule that delays or prevents the oxidation of an oxidisable target molecule. Antioxidant agents act by: scavenging biologically important reactive free radicals or other reactive oxygen species (e.g., $0^{2-}$, $H_2O_2$, HOCl, ferryl, peroxyl, peroxynitrite, and alkoxyl); preventing oxygen radical formation; or catalytically converting the free radical or other reactive oxygen species to a less reactive species.

The term "anti-inflammatory" agent as used herein refers to an active ingredient that is capable of reducing swelling, heat and redness—(conditions known as inflammation) within the body.

The terms "multivitamin", "multivitamin and mineral" or "multivitamin and multi-mineral" supplement(s) as used herein should be interpreted to mean conventional commercial type vitamin and mineral supplements prepared from specific vitamin and mineral materials.

As used herein, the term "polyvalent metal" means a metal ion having a valance of 2 or 10 higher.

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

It is apparent from the above, that the arrangements described are applicable to the healthcare, nutrition and food industries.

What is claimed is:

1. A dietary supplement composition as a prophylactic and treatment for eczema and psoriasis comprising:
   a phase II liver detoxification component having:
      Glycine in an amount of about 80-3000 mg, and
      magnesium in an amount of about 30 to 250 mg,
   nutrients including a combination of Vitamin B1 (1.1 mg), Vitamin B2 (1.1 mg), Vitamin B3 (5 mg), Pyridoxine (2 mg), Biotin (vitamin B7) (15 micrograms), Vitamin B12 (cyanocobalamin) (5 micrograms), and molybdenum in an amount of about 45 micrograms, wherein the combination of nutrients is present in a ratio range of nutrients to liver detoxification component of between about 1:12 to about 1:17;
   Vitamin C present in an amount of about 25 mg;
   Vitamin E present in an amount of about 10 mg;
   Zinc present in an amount of about 2 to about 10 mg;
   Chromium (chromium picolinate) present in an amount of about 25 micrograms; and
   fillers including flavouring agents and coloring agents and excipients.

2. A dietary supplement composition as a prophylactic and treatment eczema and psoriasis comprising:
   a component selected from a group of nutrients being effective in enhancing phase II detoxification of the liver of the patient, wherein the component is present in a majority amount of the composition, and includes a composition comprising:
      about 400 mg to 1200 mg of glycine,
      about 60 mg to at least 250 mg of Magnesium or nutritionally effective salt, and
   at least one nutrient effective for promoting a wound healing effect in vivo, wherein the at least one nutrient includes zinc as a nutritionally effective salt present in an amount of about 4 mg to 14 mg;
   at least one nutrient effective for substantially inhibiting lipoxygenase formation wherein the at least one nutrient includes vitamin E in an amount of about 20 mg; and
   at least one nutrient effective for reducing histamine levels in the patient wherein the at least one nutrient includes vitamin C in an amount of about 50 mg to 160 mg.

3. The dietary supplement composition as a prophylactic and treatment for eczema and psoriasis according to claim 2 further comprising:
   about 400 mg to 1100 mg of calcium; and
   an effective amount of at least one nutrient selected from the group of vitamins comprising of about 0.1 mg to about 10 mg vitamin B1, about 0.1 mg to about 6 mg, vitamin B2, about 1 mg to about 30 mg vitamin B3, about 0.1 mg to about 90 mg vitamin B6, about 1 mg to about 1200 mg vitamin E, about 1 µg to about 1200 ug vitamin B7, about 1 µg to about 600 µg vitamin B12, about 0.1 µg to about 100 µg vitamin D, and about 45 micrograms of molybdenum.

4. A prophylactic and treatment for eczema and psoriasis comprising:
   a first dietary supplement composition comprising:
      a phase II liver detoxification component having:
         glycine in an amount of 800 mg, and
         magnesium in an amount of 120 mg,
         nutrients including vitamin B1 in an amount of 1.2 mg, vitamin B2 in an amount of 1.2 mg, vitamin B3 in an amount of 2 mg, vitamin B6 in an amount of 2 mg, vitamin B7 in an amount of 0.03 mg, vitamin B12 in an amount of 0.01 mg, vitamin C as magnesium ascorbate in an amount of 60 mg;
      Zinc present in an amount of 8 mg;
      Molybdenum present in an amount of about 0.045 mg; and
      fillers;
   a second dietary supplement composition complementary to the first composition comprising:
      calcium present in an amount of about 1000 mg;
      magnesium present in an amount of 120 mg; and
      vitamin D3 present in an amount of about 0.02 mg;
      wherein the first and second dietary supplement compositions are administered spaced apart so as to substantially improve absorption of zinc and glycine.

5. A prophylactic and treatment for eczema and psoriasis comprising:
   a phase II liver detoxification component having:
      Glycine present in an amount of about 400-1200 mg; and
      Magnesium pre present in an amount of about 30 mg;
   at least one nutrient effective for substantially inhibiting lipoxygenase formation wherein the at least one nutrient includes vitamin E in an amount of about 10 mg;
   nutrients including vitamin B1 in an amount of 1.1 mg, vitamin B2 in an amount of 1.1 mg, vitamin B3 in an amount of 5 mg, vitamin B6 in an amount of 2 mg, vitamin B7 in an amount of 0.015 mg, vitamin B12 in an amount of 0.005 mg, vitamin C in an amount of 25 mg, molybdenum present in an amount of about 0.045 mg; and vitamin D3 in an amount of 0.005 mg;
   chromium present in an amount of about 0.025 mg to substantially modify a patient's inflammatory response by promoting conversion of DGLA to series 1 prostaglandin (PGE1);
   zinc present in an amount of about 2 to about 10 mg for enhancing a wound healing function; and
   fillers.

* * * * *